US011185497B2

(12) United States Patent
Hoekman et al.

(10) Patent No.: US 11,185,497 B2
(45) Date of Patent: Nov. 30, 2021

(54) INTRANASAL DELIVERY OF DIHYDROERGOTAMINE BY PRECISION OLFACTORY DEVICE

(71) Applicant: Impel Neuropharma, Inc., Seattle, WA (US)

(72) Inventors: John D. Hoekman, Seattle, WA (US); Kelsey H. Satterly, Seattle, WA (US); Stephen B. Shrewsbury, Fallbrook, CA (US); Scott Youmans, Bothell, WA (US); Christopher Fuller, Seattle, WA (US)

(73) Assignee: Impel Neuropharma, Inc., Seattle, WA (US)

( * ) Notice: Subject to any disclaimer, the term of this patent is extended or adjusted under 35 U.S.C. 154(b) by 0 days.

(21) Appl. No.: 17/062,364

(22) Filed: Oct. 2, 2020

(65) Prior Publication Data

US 2021/0022995 A1   Jan. 28, 2021

Related U.S. Application Data

(63) Continuation of application No. 16/240,639, filed on Jan. 4, 2019, now abandoned.
(Continued)

(51) Int. Cl.
*A61P 25/06* (2006.01)
*A61K 9/00* (2006.01)
(Continued)

(52) U.S. Cl.
CPC ............ *A61K 9/0043* (2013.01); *A61K 31/48* (2013.01); *A61K 31/522* (2013.01); *A61K 47/26* (2013.01);
(Continued)

(58) Field of Classification Search
CPC .. A61K 9/0043; A61K 31/48; A61K 15/0065; A61P 25/06
See application file for complete search history.

(56) References Cited

U.S. PATENT DOCUMENTS 2,933,259 A    4/1960  Raskin
3,157,179 A   11/1964  Paullus et al.
(Continued)

FOREIGN PATENT DOCUMENTS

BE       1006872 A     1/1995
CN    201759968 U     3/2011
(Continued)

OTHER PUBLICATIONS

U.S. Appl. No. 16/240,639, filed Jan. 2019, Hoekman et al.*
(Continued)

*Primary Examiner* — Craig D Ricci
*Assistant Examiner* — Janet L Coppins
(74) *Attorney, Agent, or Firm* — Fenwick & West LLP

(57) ABSTRACT

Methods are provided for acutely treating migraine headache with or without aura. The methods comprise administering to a subject with migraine headache an effective dose of a liquid pharmaceutical composition comprising dihydroergotamine (DHE) or a salt thereof, wherein the dose is administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml. Also provided are kits for acutely treating migraine with or without aura in which a liquid pharmaceutical composition comprising DHE or DHE salt is contained within a sealed vial that is attachable to a precision intranasal olfactory delivery device packaged therewith.

5 Claims, 19 Drawing Sheets

Related U.S. Application Data

(60) Provisional application No. 62/643,657, filed on Mar. 15, 2018, provisional application No. 62/613,939, filed on Jan. 5, 2018.

(51) Int. Cl.
*A61M 11/00* (2006.01)
*A61M 11/02* (2006.01)
*A61M 15/00* (2006.01)
*A61K 31/48* (2006.01)
*A61K 31/522* (2006.01)
*A61K 47/26* (2006.01)
*A61M 15/08* (2006.01)

(52) U.S. Cl.
CPC ........... *A61M 11/002* (2014.02); *A61M 11/02* (2013.01); *A61M 15/002* (2014.02); *A61M 15/0028* (2013.01); *A61M 15/0065* (2013.01); *A61M 15/08* (2013.01); *A61P 25/06* (2018.01)

(56) References Cited

U.S. PATENT DOCUMENTS

| | | |
|---|---|---|
| 3,425,414 A | 2/1969 | Roche |
| 3,704,812 A | 12/1972 | Marand |
| 3,741,443 A | 6/1973 | Marand |
| 3,888,253 A | 6/1975 | Watt et al. |
| 3,906,950 A | 9/1975 | Cocozza |
| 3,908,654 A | 9/1975 | Lhoest et al. |
| 3,921,857 A | 11/1975 | Riccio |
| 3,971,377 A | 7/1976 | Damani |
| 3,982,668 A | 9/1976 | Riccio |
| 4,095,596 A | 6/1978 | Grayson |
| 4,187,985 A | 2/1980 | Goth |
| 4,227,522 A | 10/1980 | Carris |
| 4,353,365 A | 10/1982 | Hallworth et al. |
| 4,412,573 A | 11/1983 | Zdeb |
| 4,462,983 A | 7/1984 | Azria et al. |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,169,849 A | 12/1992 | Kiechel et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,756,483 A | 5/1998 | Merkus |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,942,251 A | 8/1999 | Merkus |
| 5,954,696 A | 9/1999 | Ryan |
| 6,062,213 A | 5/2000 | Fuisz et al. |
| 6,092,522 A | 7/2000 | Calvert et al. |
| 6,145,703 A | 11/2000 | Opperman |
| 6,158,676 A | 12/2000 | Hughes |
| 6,180,603 B1 | 1/2001 | Frey |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey |
| 6,347,789 B1 | 2/2002 | Rock |
| 6,367,471 B1 | 4/2002 | Genosar et al. |
| 6,367,473 B1 | 4/2002 | Käfer |
| 6,382,465 B1 | 5/2002 | Greiner Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Gañán Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,597,216 B2 | 10/2009 | Behar et al. |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,148,377 B2 | 4/2012 | Cook et al. |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,978,647 B2 | 3/2015 | Djupesland et al. |

(56) References Cited

U.S. PATENT DOCUMENTS

| | | |
|---|---|---|
| 8,987,199 B2 | 3/2015 | Abdel Maksoud et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 9,550,036 B2 | 1/2017 | Hoekman et al. |
| 9,649,456 B2 | 5/2017 | Djupesland et al. |
| 9,833,451 B2 | 12/2017 | Cook et al. |
| 2002/0017294 A1 | 2/2002 | Py |
| 2002/0054856 A1 | 5/2002 | Jones |
| 2002/0092520 A1 | 7/2002 | Casper et al. |
| 2003/0017119 A1 | 1/2003 | Rabinowitz et al. |
| 2003/0091513 A1 | 5/2003 | Mohsen et al. |
| 2003/0114476 A1 | 6/2003 | Plachetka et al. |
| 2003/0158527 A1 | 8/2003 | Mezzoli |
| 2003/0198669 A1 | 10/2003 | Cutler et al. |
| 2003/0217748 A1 | 11/2003 | Giroux |
| 2004/0068222 A1 | 4/2004 | Brian |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0147389 A1 | 7/2006 | Staniforth et al. |
| 2006/0219813 A1 | 10/2006 | Morrison |
| 2006/0240092 A1 | 10/2006 | Breitenkamp et al. |
| 2006/0246070 A1 | 11/2006 | Heavner et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Ben Sasson et al. |
| 2007/0202051 A1 | 8/2007 | Schuschnig |
| 2007/0253913 A1 | 11/2007 | Mohsen et al. |
| 2008/0017190 A1 | 1/2008 | Anandampillai et al. |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0223363 A1 | 9/2008 | Djupesland |
| 2008/0305077 A1 | 12/2008 | Frey et al. |
| 2009/0216183 A1 | 8/2009 | Minotti |
| 2009/0320832 A1 | 12/2009 | Djupestand |
| 2010/0081663 A1 | 4/2010 | Cook et al. |
| 2010/0199984 A1 | 8/2010 | Williams, III et al. |
| 2010/0242958 A1 | 9/2010 | Jinks et al. |
| 2011/0045088 A1 | 2/2011 | Tsutsui et al. |
| 2011/0053859 A1 | 3/2011 | Deadwyler et al. |
| 2012/0195959 A1 | 8/2012 | Ishii |
| 2013/0180524 A1 | 7/2013 | Shahaf et al. |
| 2013/0327323 A1 | 12/2013 | Rubin |
| 2014/0014104 A1 | 1/2014 | Hoekman et al. |
| 2014/0034051 A1 | 2/2014 | Addington et al. |
| 2014/0083424 A1 | 3/2014 | Hoekman et al. |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0216823 A1 | 8/2015 | Chatterjee |
| 2015/0258178 A1 | 9/2015 | Gong |
| 2016/0101245 A1 | 4/2016 | Hoekman et al. |
| 2016/0228433 A1 | 8/2016 | Haruta et al. |
| 2016/0367771 A1 | 12/2016 | Djupesland |
| 2017/0043109 A1 | 2/2017 | Hoekman et al. |
| 2017/0196861 A1 | 7/2017 | Cook et al. |
| 2018/0360110 A1 | 12/2018 | Marsot et al. |
| 2019/0000753 A1 | 1/2019 | Narasimha Murthy et al. |
| 2019/0001088 A1 | 1/2019 | Petit |
| 2019/0275036 A1 | 9/2019 | Haruta et al. |
| 2020/0179379 A1 | 6/2020 | Haruta et al. |

FOREIGN PATENT DOCUMENTS

| | | |
|---|---|---|
| CN | 202263268 U | 6/2012 |
| CN | 203139302 U | 8/2013 |
| DE | 19518580 A1 | 11/1996 |
| DE | 102013100473 A1 | 7/2014 |
| EP | 0689438 A1 | 1/1996 |
| EP | 0865789 A3 | 1/1999 |
| EP | 1165044 A2 | 1/2002 |
| EP | 1165044 B1 | 6/2004 |
| GB | 806284 A | 12/1958 |
| GB | 1493614 A | 11/1977 |
| GB | 1517642 A | 7/1978 |
| JP | S 50-78912 A | 6/1975 |
| JP | H08322934 A | 12/1996 |
| JP | 2014-530637 A | 11/2014 |
| WO | WO 1986/001731 A1 | 3/1986 |
| WO | WO 9422445 A2 | 10/1994 |
| WO | WO 1999/013930 A1 | 3/1999 |
| WO | WO 2000/054887 A1 | 9/2000 |
| WO | WO 2001/036033 A2 | 5/2001 |
| WO | WO 2002/009707 A1 | 2/2002 |
| WO | WO 03/106840 A2 | 12/2003 |
| WO | WO-2005/025506 A3 | 3/2006 |
| WO | WO 2007/012853 A1 | 2/2007 |
| WO | WO 2007/081948 A2 | 7/2007 |
| WO | WO 2007/081948 A3 | 4/2008 |
| WO | WO 2008/059385 A2 | 5/2008 |
| WO | WO 2012/119153 A2 | 9/2012 |
| WO | WO 2015/044782 A2 | 4/2015 |
| WO | WO 2017/044897 A1 | 3/2017 |
| WO | WO 2018/025089 A2 | 2/2018 |
| WO | WO 2019/008439 A1 | 1/2019 |

OTHER PUBLICATIONS

Van der Kuy et al, Eur J Clin Pharmacol (1999), vol. 55, pp. 677-680. (Year: 1999).*

Djupesland, Per Gisle. Drug Deliv and Transl. Res. (2013), vol. 3. pp. 42-62. (Year: 2013).*

Righton, Louise, Manufacturing Chemist, Sep. 2014. pp. xi-xiii. (Year: 2014).*

Humbert et al, Clinical Pharmacology & Therapeutics, Sep. 1996, vol. 60(3). pp. 265-275. (Year: 1996).*

Appasaheb, et al., "Review on Intranasal Drug Delilvery System", Journal of Advanced Pharmacy Education and Research, vol. 3, Issue 4, Oct. 2013, 14 pages.

Aurora, S. K. et al., "A Randomized, Double Blind, Placebo-Controlled Study of MAP0004 in Adult Patients With Migraine," Headache, Jun. 2009, pp. 826-837, vol. 49, No. 6.

Australian New Zealand Clinical Trials Registry, "A Phase I, Comparative Bioavailability Study of Dihydroergotamine Mesylate (DHE) Administered by I123 Precision Olfactory Delivery (PODTM) Device Nasal Spray, DHE for Injection (Intravenous), and Migranal® Nasal Spray in Healthy Male and Female adult Subjects," 2017, 7 pages.

Baron, "Orally Inhaled Dihydroergotamine; Reviving and Improving a Classic", Future Neurology, May 2011, 11 pages.

Constantino, et al., "Intranasal administration of acetylcholinesterase inhibitors", BMC Neuroscience, Dec. 10, 2008, 3 pages.

Cook, R. O. et al., "Reduced Adverse Event Profile of Orally Inhaled DHE (MAP0004) vs IV DHE: Potential Mechanism," Headache, Nov./Dec. 2009, pp. 1423-1434, vol. 49, No. 10.

"D.H.E. 45 (dihydroergotamine mesylate) Injection, USP," Valeant Pharmaceuticals North America, Aug. 2008, 16 pages.

European Patent Office, EP Office Action for 14727320.5, dated Nov. 9, 2016, 6 pages.

European Patent Office, EP Search Report for 09707800.0 dated Jul. 1, 2015, 12 pages.

European Patent Office, EP Search Report for 11818832.5 dated Sep. 24, 2014, 6 pages.

(56) References Cited

OTHER PUBLICATIONS

European Patent Office, Supplementary European Search Report, European Patent Application No. 16845229, dated Apr. 9, 2019, 8 pages.

Hanson, et al., "Intranasal delivery of growth differentiation factor 5 to the central nervous system", Drug Delivery, 19(3):149-54, Feb. 2012, 7 pages.

Headache Classification Committee of the International Headache Society (IHS), "The International Classification of Headache Disorders, $3^{rd}$ edition," Cephalalgia, 2018, 211 pages, vol. 38, No. 1.

Hoekman, J.D., "The Impact of Enhanced Olfactory Deposition and Retention on Direct Nose-to-Brain Drug Delivery", UMI Dissertation Publishing, Apr. 11, 2011, 181 pages.

Humbert, H. et al., "Human pharmacokinetics of dihydroergotamine administered by nasal spray," Clinical Pharmacology & Therapeutics, Sep. 1996, p. 265-275, vol. 60, No. 3.

Impel Neuropharma, "Migraine Treatment," Apr. 29, 2016, three pages, [Online] [Retrieved on Jul. 19, 2017], Retrieved from the Internet <URL: http://web.archive.org/web/20160429165231/impelnp.com/migraine-treatment/>.

Impel Neuropharma, "POD Technology," Apr. 29, 2016, four pages, [Online] [Retrieved on Jul. 19, 2017], Retrieved from the Internet <URL: http://web.archive.org/web/20160429165242/http://impelnp.com:80/pod-technology/>.

Intellectual Property India Patent Application No. IN 201741000065, filed Jul. 2, 2017, Applicant: Dr. Reddy's Laboratories Limited.

Iwashima, F. et al., "STS101 (Dry Powder Intranasal Dihydroergotamine) Drug-Device Combination Achieves Consistent and Robust Delivery Performance for Migraine Patients," International Headache Conference, Sep. 5-8, 2019, one page.

Japan Patent Office, Official Notice of Rejection, JP Patent Application No. 2018-513344, dated Apr. 7, 2020, nine pages.

Kellerman, D. J. et al., "Assessment of the Consistency of Absorption of Dihydroergotamine Following Oral Inhalation: Pooled results from Four Clinical Studies," Journal of Aerosol Medicine and Pulmonary Drug Delivery, 2013, pp. 297-306, vol. 26, No. 5.

Kumar, et al., "Nasal Drug Delivery: A Potential Route for Brain Targeting" The Pharma Innovation Journal, vol. 2, No. 1, Mar. 2013, 9 pages.

"Make the Most of MIGRANAL: Administration Instructions: How to Use MIGRANAL Nasal Spray," MIGRANAL Nasal Spray, Valeant Pharmaceuticals International, Inc., 2016, 7 pages.

Mauskop, A., "Getting medicine straight from the nose to the brain," Headache NewsBlog, Jan. 6, 2013, two pages, [Online] [Retrieved on Jun. 23, 2017], Retrieved from the Internet <URL: https://www.nyheadache.com/blog/getting-medicine-straight-from-the-nose-to-the-brain/>.

Mauskop, A., "Getting medicine straight from the nose to the brain," New York Headache blog, Jan. 6, 2013, 2 pages, [Online], [Retrieved Jun. 23, 2017], Retrieved from the Internet: <URL:https://www.nyheadache.com/blog/getting-medicine-straight-from-the-nose-to-the-brain/>.

"Migranal Product Label," Valeant Pharmaceuticals North America LLC, Nov. 2014, six pages.

Nih, "A Phase I Study to Study the PK and Safety of Single Doses of STS101, DHE Injection and Nasal Spray in Healthy Subjects," U.S. National Library of Medicine, ClinicalTrials.gov, Mar. 14, 2019, seven pages, [Online] [Retrieved on Dec. 24, 2019], Retrieved from the Internet <URL: https://clinicaltrials.gov/ct2/show/NCT03874832>.

Nih, "A Randomized, Double-Blind, Placebo-Controlled Study to Evaluate STS101 in the Acute Treatment of Migraine (EMERGE)," U.S. National Library of Medicine, ClinicalTrials.gov, Apr. 3, 2019, seven pages, [Online] [Retrieved on Dec. 24, 2019], Retrieved from the Internet <URL: https://clinicaltrials.gov/ct2/show/NCT03901482>.

Ozsoy, et al., "Nasal Delivery of High Molecular Weight Drugs", Molecules Journal, Sep. 23, 2009, 26 pages.

Parvathi, "Intranasal Drug Delivery to Brain: An Overview," published in the International Journal of Research in Pharmacy and Chemistry 2012, 2(3), 7 pages.

PCT International Search Report, PCT Application No. PCT/US/2009/033468 dated Dec. 2, 2009, 5 pages.

PCT International Preliminary Report on Patentability, PCT Application No. PCT/US2016/051169, dated Mar. 29, 2018, six pages.

PCT International Search Report and Written Opinion, PCT Application No. PCT/US2016/051169, dated Jan. 26, 2017, nine pages.

PCT International Search Report, PCT Application No. PCT/IB2014/002706, dated Mar. 20, 2015, four pages.

PCT Search Report and Written Opinion, PCT Application No. PCT/US2011/048435, dated Mar. 27, 2012, 14 pages.

PCT Invitation to Pay Additional Fees and, where Applicable, Protest Fee, PCT Application No. PCT/US2019/012405, dated Mar. 4, 2019, two pages.

Renner, et al., "Intranasal delivery of growth differentiation factor 5 to the central nervous system," Drug Delivery, Feb. 2012, 7 pages.

Saper, J. R. et al., "Pharmacology of Dihydroergotamine and Evidence for Efficacy and Safety in Migraine," Headache, Nov. 2006, pp. S171-S181, vol. 46, No. S4.

Shrewsbury, S. B. et al., "Intrapulmonary and intravenous administrations of dihydroergotamine mesylate have similar cardiovascular effects in the conscious dog," British Journal of Pharmacology, Jul. 2008, pp. 1254-1265, vol. 154, No. 6.

Shrewsbury, S. B. et al., "Randomized, double-blind, placebo-controlled study of the safety, tolerability and pharmacokinetics of MAP0004 (orally-inhaled DHE) in adult asthmatics," Current Medical Research and Opinion, 2008, pp. 1977-1985, vol. 24, No. 7.

Shrewsbury, S. B. et al., "Safety and Pharmacokinetics of Dihydroergotamine Mesylate Administered Via a Novel (Tempo™) Inhaler," Headache, Mar. 2008, pp. 355-367, vol. 48, No. 3.

Shrewsbury, S. B. et al., "STOP 101: A Phase 1, Randomized, Open-Label, Comparative Bioavailability Study of INP104, Dihydroergotamine Mesylate (DHE) Administered Intranasally by a I123 Precision Olfactory Delivery (POD®) Device, in Healthy Adult Subjects,' Headache, Mar. 2019, 16 pages, vol. 59, No. 3.

Shrewsbury, S.B. et al., "Intrapulmonary and intravenous administrations of dihydroergotamine mesylate have similar cardiovascular effects in the conscious dog," Nature Publishing Group, 2008, vol. 154, No. 6, 12 pages.

Shrewsbury, S.B., et al., "Safety, Tolerability and Comparative Bioavailability of a Novel Intranasal DHE Product (INP104)," Impel Neuropharma, American Headache Society 60th Annual Meeting, 2018, 1 page.

Silberstein, S.D. et al., "Dihydroergotamine: a review of formulation approaches for the acute treatment of migraine," CNS Drugs, 2013, pp. 385-394, vol. 27, No. 5.

Silberstein, S. D. et al., "Dihydroergotamine (DHE)—Then and Now: A Narrative Review," Headache, 2019, 18 pages.

Silberstein, S.D., et al., "Ergotamine and dihydroergotamine: history, pharmacology, and efficacy," Headache: The Journal of Head and Face Pain, 2003, vol. 43, No. 2, pp. 144-166.

Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.

Strom, S. et al., "Comparison of the Pharmacokinetics of STS101, an Intranasal Dry Power Formulation of Dihydroergotamine, with Other Intranasal, Injectable, and Oral Inhaled DHE Formulations," International Headache Conference, Sep. 5-8, 2019, one page.

Talegaonkar, et al., "Intranasal delivery: an approach to bypass the blook brain barrier", Indian J Pharmacol, Jun. 2004, vol. 36, Issue 3, 8 pages.

The Patent Office of the People's Republic of China, First Office Action, CN Patent Application No. 201680060459.8, dated Apr. 14, 2020, 22 pages.

Van Der Kuy, P-H. M. et al., "Bioavailability of intranasal formulations of dihydroergotamine," European Journal of Clinical Pharmacology, Nov. 1999, pp. 677-680, vol. 55, No. 9.

Wang, Y. et al., Abstract of "Brain uptake of dihydroergotamine after intravenous and nasal administration in the rat," Biopharm Drug Dispos., Dec. 1998, two pages, [Online] [Retrieved on Jul. 18, 2017], Retrieved from the Internet <URL: https://pubmed.ncbi.nlm.nih.gov/9872338/>.

(56) References Cited

OTHER PUBLICATIONS

Westin et al, "Direct Nose to Brain Transfer of Morphine After Nasal Administration to Rats", Pharmaceutical Research, vol. 23, No. 3, Mar. 2006, 8 pgs.
Westin, "Olfactory Transfer of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medicine, 3(1), Jan. 2008, 4 pages.
Zhang, et al, "The brain targeting efficiency following nasally applied MPEG-PLA nanoparticles in rats", Journal of Drug Targeting, Jun. 2006, 11 pages.
China National Intellectual Property Administration, Notice of Allowance, Chinese Patent Application No. 201680060459.8, dated May 8, 2021, three pages (with concise explanation of relevance).
China National Intellectual Property Administration, Search Report, Chinese Patent Application No. 201680060459.8, dated Apr. 15, 2021, six pages.

\* cited by examiner

SECTION A-A

# INTRANASAL DELIVERY OF DIHYDROERGOTAMINE BY PRECISION OLFACTORY DEVICE

1. CROSS-REFERENCE TO RELATED APPLICATIONS

This application is a continuation of U.S. application Ser. No. 16/240,639 filed Jan. 4, 2019, which claims priority to U.S. provisional application Nos. 62/643,657, filed Mar. 15, 2018, and 62/613,939, filed Jan. 5, 2018, each of which is incorporated herein by reference in its entirety.

2. BACKGROUND

Dihydroergotamine (DHE), a semisynthetic derivative of the ergot alkaloid ergotamine, has been approved for over 70 years for the treatment of migraines. The exact mechanism of action of DHE is not known, but DHE is known to act as a serotonin receptor agonist, cause vasoconstriction of intracranial blood vessels, and interact centrally with dopamine and adrenergic receptors.

The oral bioavailability of DHE is poor, and DHE is commonly administered parenterally as the mesylate salt by subcutaneous, intramuscular or intravenous injection, and where approved, by nasal spray. Because migraine headaches are episodic and occur unpredictably, administration by nasal spray is far more convenient for treatment of acute migraine than is administration by injection. However, the previously approved nasal spray drug-device combination product provides only 32% of the bioavailability of the intravenous injection, and variable efficacy (among other factors) has led to its withdrawal from market in the EU and other countries, although it remains available in the United States.

There is, therefore, a need for an intranasal DHE product that provides increased bioavailability and reduced variability in systemically delivered dose for treatment of migraine.

3. SUMMARY

We designed a manually actuated, propellant-driven, intranasal administration device that can reproducibly deliver metered doses of liquid pharmaceutical compositions beyond the nasal valve to more distal regions of the nasal cavity. We tested the device in a Phase I clinical trial that compared the bioavailability of (i) dihydroergotamine (DHE) mesylate administered as a single divided 1.45 mg intranasal dose using our Precision Olfactory Delivery (POD®) Device ("INP104"); (ii) a 2.0 mg dose of DHE mesylate administered intranasally using Migranal® Nasal Spray according to the US FDA approved product label; and (iii) a 1.0 mg intravenous injection of DHE mesylate for injection (D.H.E. 45®), in healthy adult subjects.

As described in detail in Example 2, INP104 provided 4-fold higher mean maximal plasma concentration, nearly 3-fold higher mean systemic drug exposure, and reached maximal DHE plasma concentration faster than Migranal®. The higher maximal plasma concentration and systemic drug exposure were achieved with a lower administered dose of the identical formulation of DHE mesylate, 1.45 mg for INP104 versus 2.0 mg for Migranal®, and without requiring a 15-minute wait between administration of divided sub-doses, as required for Migranal®. In addition, systemic delivery of DHE was more consistent with INP104 than with Migranal®, with lower coefficient of variation (CV %) in DHE $AUC_{0-inf}$ and $C_{max}$ observed across subjects.

Accordingly, in a first aspect, methods are provided for acutely treating migraine headache with or without aura. The methods comprise administering to a subject with migraine headache an effective dose of a liquid pharmaceutical composition comprising dihydroergotamine (DHE) or a salt thereof, wherein the dose is administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml.

In various embodiments, the dose is no more than 2.0 mg DHE or salt thereof, less than 2.0 mg DHE or salt thereof, 1.2-1.8 mg DHE or salt thereof, or 1.4-1.6 mg DHE or salt thereof. In a particular embodiment, the dose is about 1.45 mg DHE or salt thereof.

In a variety of embodiments, the dose is administered as a plurality of divided doses. In certain embodiments, the dose is administered as two divided doses. In a particular embodiment, one divided dose is administered to each nostril. In typical divided dose embodiments, the dose is administered over no more than 1 minute, over no more than 45 seconds, or over no more than 30 seconds. In various embodiments, the volume of liquid composition administered per divided dose is 140-250 µL, 175 µL-225 µL, about 200 µL, or about 180 µL.

In typical embodiments, the liquid composition comprises a salt of DHE. In currently preferred embodiments, the liquid composition comprises DHE mesylate. In certain embodiments, the liquid composition comprises DHE mesylate at a concentration of 2.5-7.5 mg/ml, 3.5-6.5 mg/ml, or more particularly, 4.0 mg/ml DHE mesylate.

In some embodiments, the liquid composition further comprises caffeine. In particular embodiments, the liquid composition comprises caffeine at a concentration of 10 mg/ml. In some embodiments, the liquid composition further comprises dextrose, and in certain embodiments, dextrose at a concentration of 50 mg/ml. In specific embodiments, the liquid composition comprises 4.0 mg/ml DHE mesylate, 10.0 mg/ml caffeine, and 50 mg/ml dextrose.

In various embodiments, following administration of the dose, the mean $C_{max}$ of DHE is at least 1000 pg/ml, or at least 1200 pg/ml. In various embodiments, following administration of the dose, the mean plasma $AUC_{0-inf}$ of DHE is at least 3000 pg*hr/ml, 4000 pg*hr/ml, 5000 pg*hr/ml, or 6000 pg*hr/ml.

In some embodiments, following administration of the dose, the mean peak plasma concentration ($C_{max}$) of 8'-OH-DHE is at least 50 pg/ml or at least 55 pg/ml. In some embodiments, following administration of the dose, the mean plasma $AUC_{0-inf}$ of 8'-OH-DHE is at least 1000 pg*hr/ml.

In typical embodiments, the intranasal delivery device is a manually actuated, propellant-driven, metered-dose intranasal administration device. In some embodiments, prior to first manual actuation, the liquid pharmaceutical composition and propellant are not in contact within the device. In certain embodiments, the liquid pharmaceutical composition is contained in a vial and the propellant is contained in a canister. The canister may further be a pressurized canister. In currently preferred embodiments, between successive manual actuations, the liquid pharmaceutical composition in the vial and propellant in the canister are not in contact within the device.

In certain of these embodiments, each manual actuation brings a metered volume of liquid pharmaceutical composition and a separately metered volume of propellant into contact within a dose chamber of the device. In specific embodiments, contact of propellant with liquid pharmaceutical composition within the dose chamber of the device creates a spray of liquid pharmaceutical composition as the formulation is expelled through a nozzle of the device. In particular embodiments, the nozzle has a plurality of lumens, and the spray is ejected simultaneously through a plurality of nozzle lumens. In some embodiments, the propellant is a hydrofluoroalkane propellant, and in specific embodiments, the propellant is hydrofluoroalkane-134a.

In various embodiments, prior to first actuation, the vial is nonintegral to the device and is configured to be attachable thereto. In some of these embodiments, the vial is configured to be threadably attachable to the device.

In some embodiments, the subject has migraine headache with aura. In some embodiments, the subject has migraine headache without aura. In some embodiments, the subject has had onset of at least one prodromal symptom of migraine. In a variety of embodiments, the subject has menstrual-associated migraine. In certain embodiments, the subject has triptan-resistant migraine.

In typical embodiments, the subject self-administers the liquid pharmaceutical composition.

In a second, related, aspect, improved methods of acutely treating migraine headache with or without aura by intranasal administration of dihydroergotamine (DHE) or salt thereof are provided. In this aspect, the improvement comprises administering a dose of a liquid pharmaceutical composition comprising dihydroergotamine (DHE) or salt thereof by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0\text{-}inf}$ of DHE of at least 2500 pg*hr/ml.

In typical embodiments of this aspect, the intranasal delivery device is a manually actuated, metered-dose, propellant-driven intranasal administration device as used in methods of the first aspect. In certain embodiments, contact of propellant with liquid pharmaceutical composition within a dose chamber of the device ejects a spray of liquid pharmaceutical composition through a nozzle of the device. In specific embodiments, the nozzle has a plurality of lumens, and the spray is ejected simultaneously through a plurality of nozzle lumens.

In another aspect, kits are provided for acutely treating migraine with or without aura. The kits comprise a vial, within which is sealably contained at least one effective dose of a liquid pharmaceutical composition comprising dihydroergotamine (DHE) or salt thereof, and a device, wherein the vial is configured to be attachable to the device, and wherein the device, upon attachment of the vial, is a manually actuated, metered-dose, propellant-driven intranasal administration device capable of providing, after intranasal administration of a dose of liquid pharmaceutical composition, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0\text{-}inf}$ of DHE of at least 2500 pg*hr/ml.

In some embodiments, the device within the kit comprises a canister, wherein the canister is a pressurized canister containing propellant.

In certain of these embodiments, following attachment of the vial to the device and prior to first manual actuation, the liquid pharmaceutical composition and propellant are not in contact within the device. In some embodiments, between successive manual actuations, the liquid pharmaceutical composition in the vial and propellant in the canister are not in contact within the device. In typical embodiments, each manual actuation brings a metered volume of liquid pharmaceutical composition and a separately metered volume of propellant into contact within a dose chamber of the device, and contact of propellant with liquid pharmaceutical composition within the dose chamber of the device creates a spray of liquid pharmaceutical composition as the formulation is expelled through a nozzle of the device.

In some currently preferred embodiments, the liquid pharmaceutical composition within the vial comprises a salt of DHE. In certain embodiments, the liquid composition comprises DHE mesylate. In particular embodiments, the liquid composition comprises DHE mesylate at a concentration of 2.5-7.5 mg/ml, or about 4.0 mg/ml DHE mesylate. In specific embodiments, the liquid composition comprises 4.0 mg/ml DHE mesylate, 10.0 mg/ml caffeine, and 50 mg/ml dextrose.

In various kit embodiments, the vial contains no more than 2 ml of liquid pharmaceutical composition. In some embodiments, the vial contains approximately 1 ml of liquid pharmaceutical composition.

In some embodiments, the pressurized canister contains an amount of propellant sufficient to administer no more than 1 dose of liquid pharmaceutical composition.

Other features and advantages of the present disclosure will become apparent from the following detailed description, including the drawings. It should be understood, however, that the detailed description and the specific examples are provided for illustration only, because various changes and modifications within the spirit and scope of the invention will become apparent to those skilled in the art from the detailed description.

4. BRIEF DESCRIPTION OF THE DRAWINGS

FIG. 2A shows the in-line nasal delivery device at rest with FIG. 2B showing the actuation of the pump and FIG. 2C showing actuation of the propellant valve.

Figure 10A:
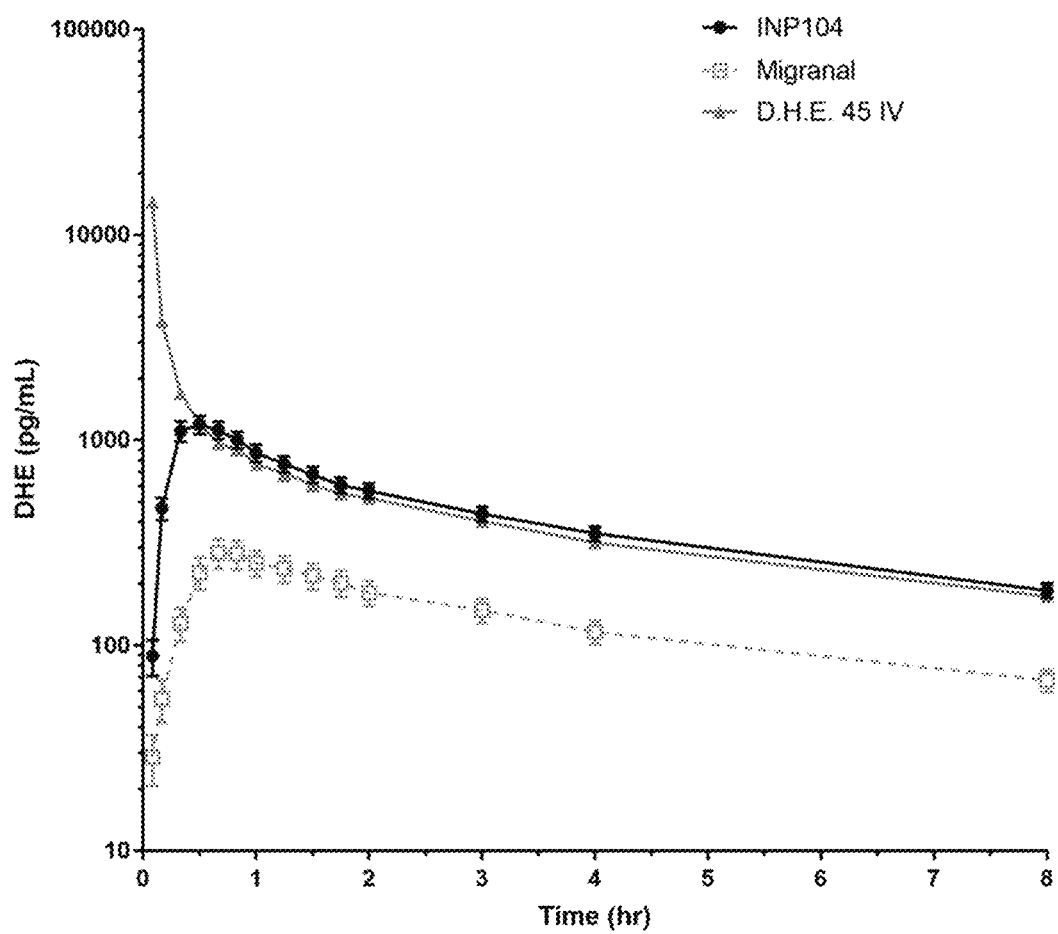
Figure 10B:
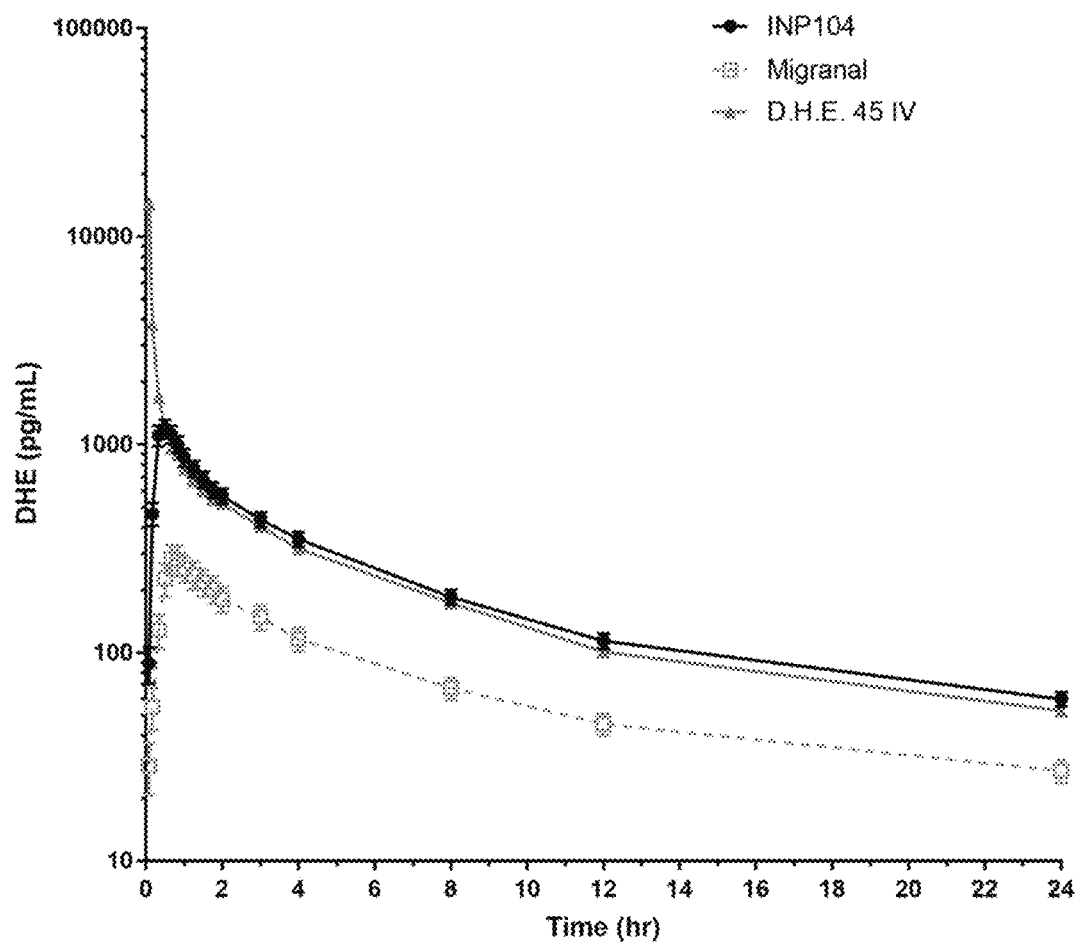

FIGS. 10A and 10B plot plasma concentrations of DHE versus time as measured in the phase I comparative bioavailability clinical trial described in Example 2, with FIG. 10A plotting data from 0 to 8 hours and FIG. 10B plotting data from 0 to 24 hours.

Figure 11A:
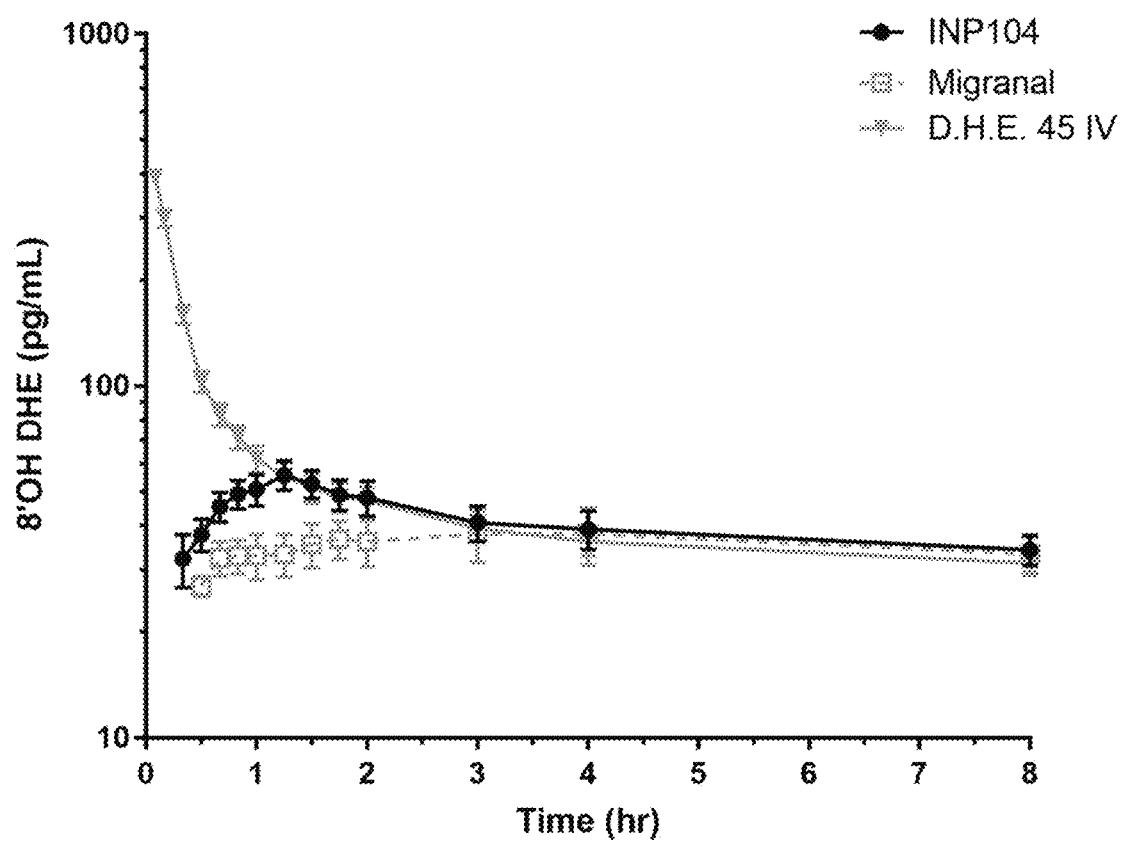
Figure 11B:
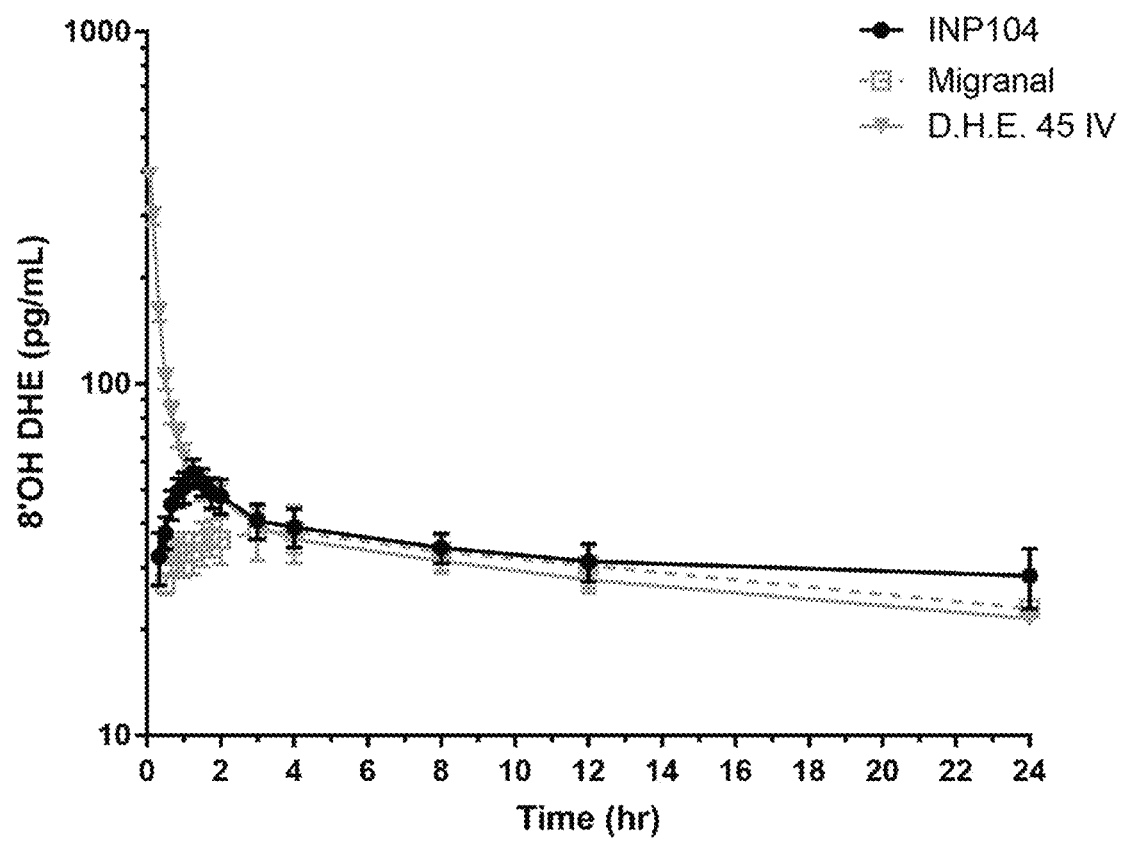

FIGS. 11A and 11B plot plasma concentrations of the 8'-OH-DHE metabolite of DHE versus time as measured in the phase I comparative bioavailability clinical trial described in Example 2, with FIG. 11A plotting data from 0 to 8 hours and FIG. 11B plotting data from 0 to 24 hours.

Figure 12A:
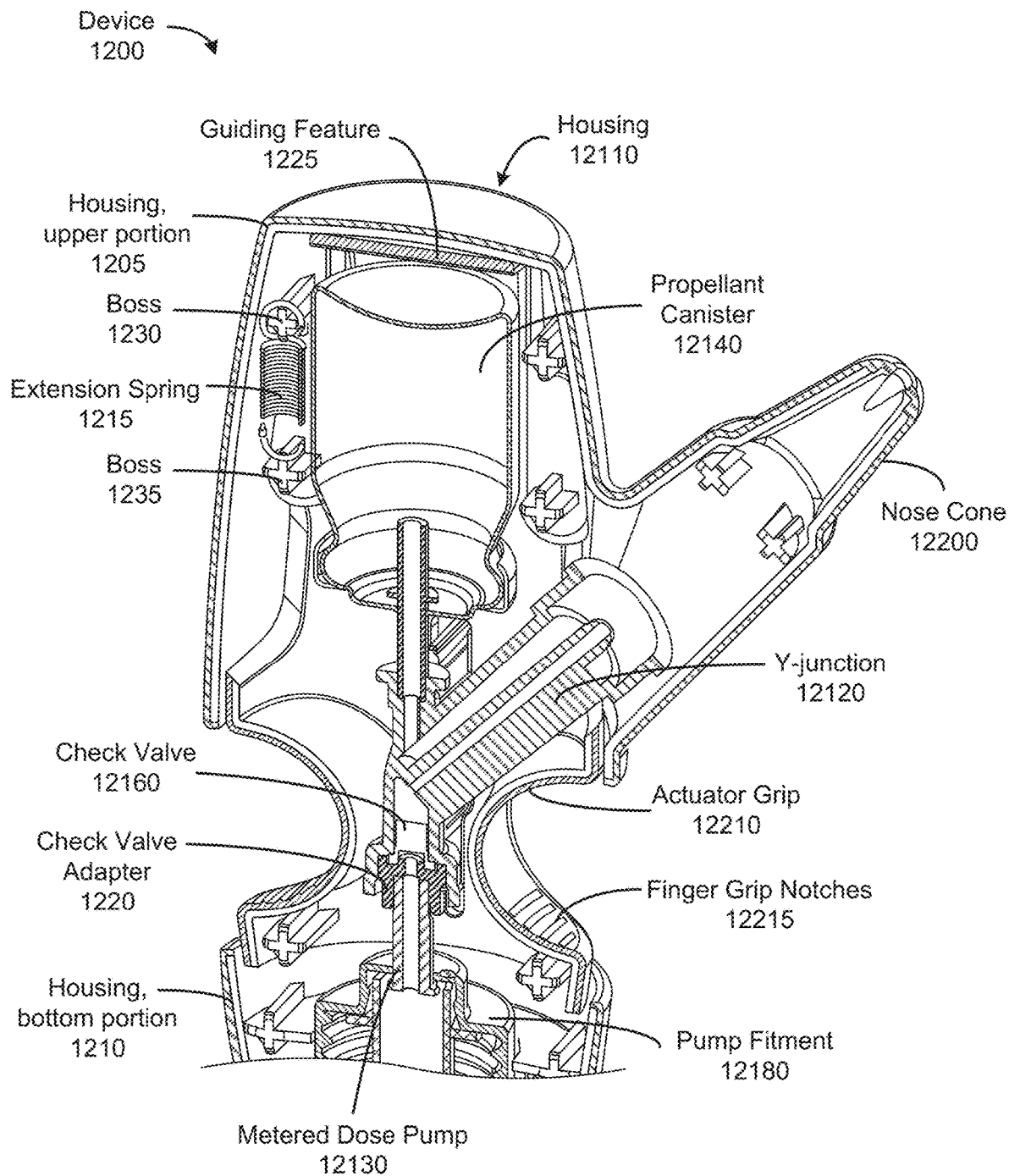

FIG. 12A shows a cross section of an alternate implementation of the in-line nasal delivery device.

Figure 12B:
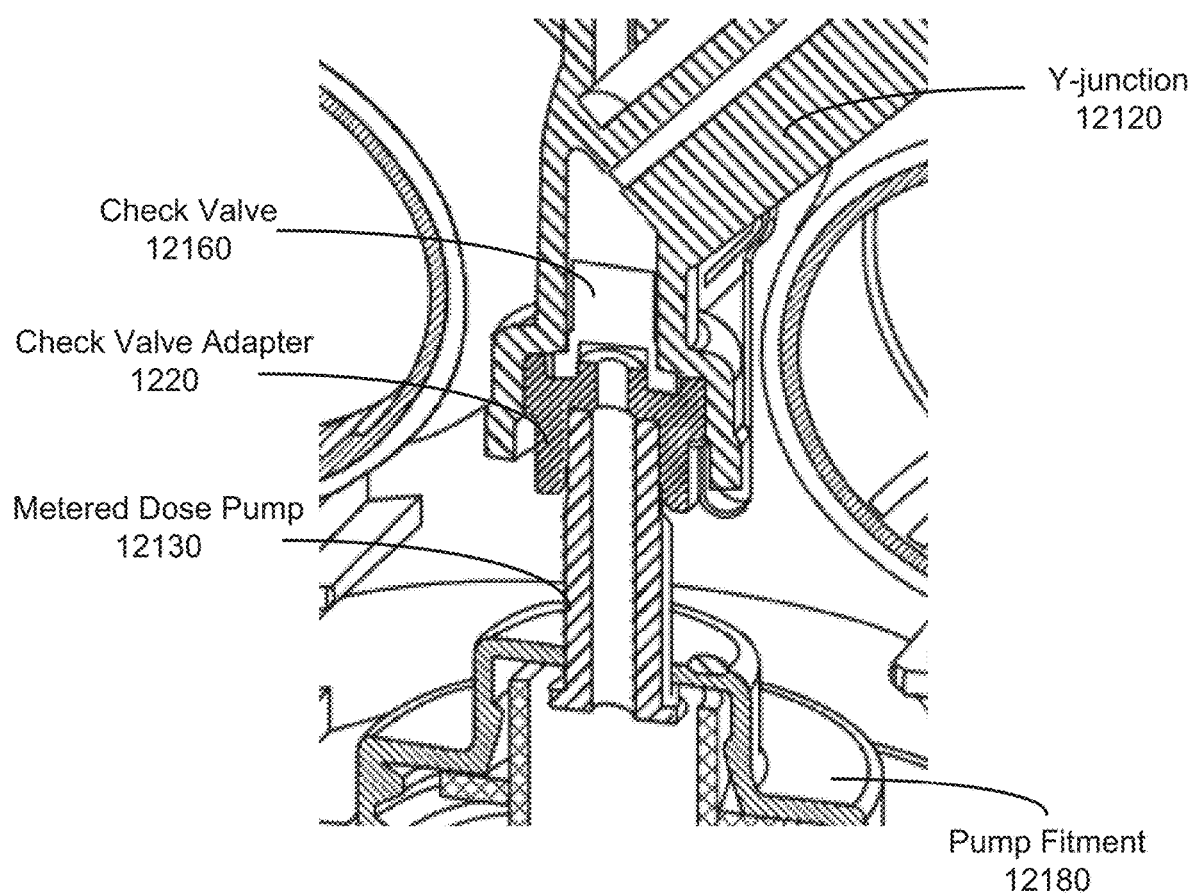

FIG. 12B shows a zoomed-in view of the cross section of FIG. 12A.

Figure 13A:
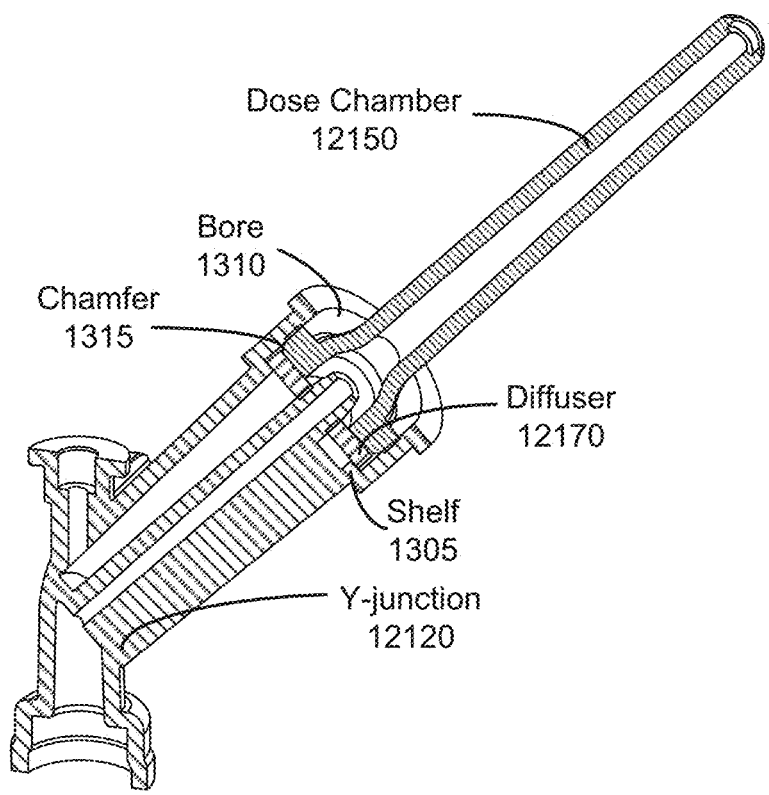

FIG. 13A shows a cross section of the diffuser as seated within the device, according to an additional embodiment.

Figure 13B:
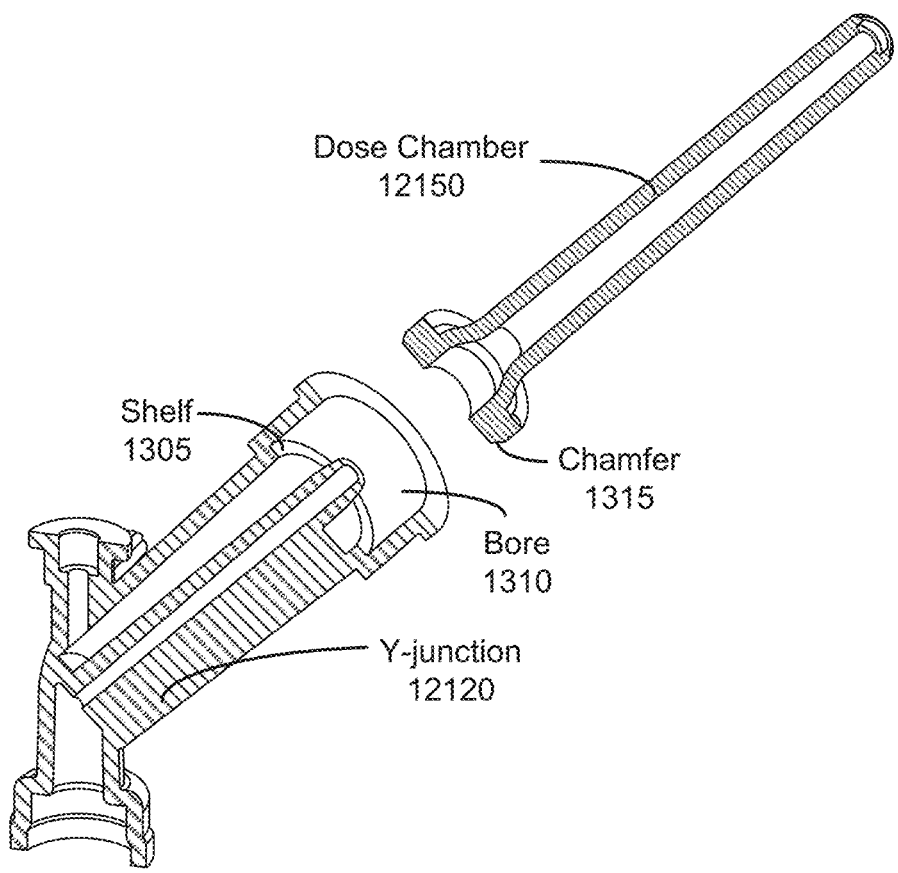

FIG. 13B shows an exploded view of the nozzle and the Y-junction, according to an additional embodiment.

Figure 14:
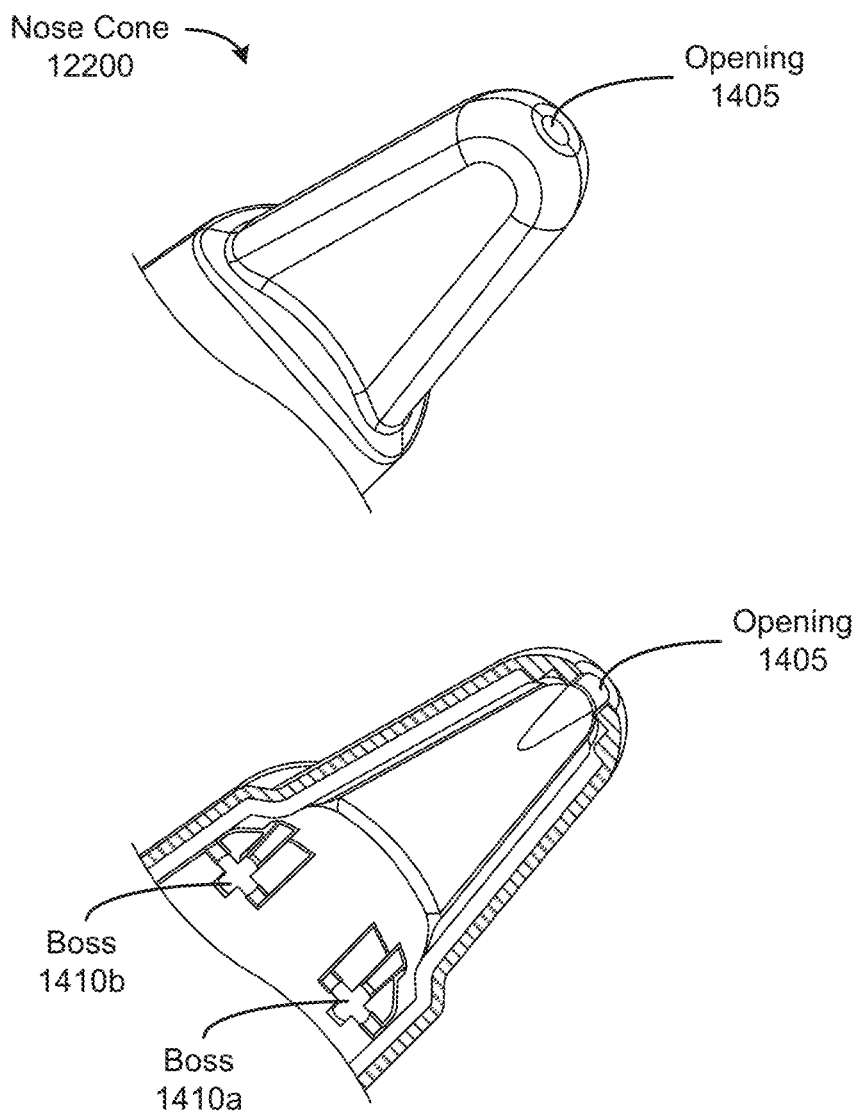

FIG. 14 illustrates the nose cone, according to an additional embodiment.

5. DETAILED DESCRIPTION

5.1. Definitions

Unless defined otherwise, all technical and scientific terms used herein have the meaning commonly understood by a person skilled in the art to which this invention belongs.

5.2. Other Interpretational Conventions

Ranges: throughout this disclosure, various aspects of the invention are presented in a range format. Ranges include the recited endpoints. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Unless specifically stated or apparent from context, as used herein the term "or" is understood to be inclusive.

Unless specifically stated or apparent from context, as used herein, the terms "a", "an", and "the" are understood to be singular or plural. That is, the articles "a" and "an" are used herein to refer to one or to more than one (i.e., to at least one) of the grammatical object of the article. By way of example, "an element" means one element or more than one element.

In this disclosure, "comprises," "comprising," "containing," "having," "includes," "including," and linguistic variants thereof have the meaning ascribed to them in U.S. Patent law, permitting the presence of additional components beyond those explicitly recited.

Unless specifically stated or otherwise apparent from context, as used herein the term "about" is understood as within a range of normal tolerance in the art, for example within 2 standard deviations of the mean and is meant to encompass variations of ±20% or ±10%, more preferably ±5%, even more preferably ±1%, and still more preferably ±0.1% from the stated value.

5.3. Summary of Experimental Observations

We designed a manually actuated, propellant-driven, intranasal administration device that can reproducibly deliver metered doses of liquid pharmaceutical compositions beyond the nasal valve to more distal regions of the nasal cavity. We tested the device in a Phase I clinical trial designed to compare the bioavailability of (i) dihydroergotamine (DHE) mesylate administered as a single divided 1.45 mg intranasal dose using this Precision Olfactory Delivery (POD™) Device ("INP104"); (ii) a 2.0 mg dose of DHE mesylate administered intranasally using Migranal® Nasal Spray according to the US FDA approved product label; and (iii) a 1.0 mg intravenous injection of DHE mesylate for injection (D.H.E. 45®), in healthy adult subjects.

As described in detail in Example 2, INP104 provided nearly 3-fold higher mean systemic drug exposure, nearly 4-fold higher mean maximal plasma concentration, and reached maximal DHE plasma concentration faster than Migranal®. The higher systemic drug exposure and higher maximal plasma concentration were achieved with a lower administered dose of the identical formulation of DHE mesylate, 1.45 mg for INP104 versus 2.0 mg for Migranal®, and without requiring a 15-minute wait between administration of divided sub-doses, as required for Migranal®.

In addition, systemic delivery of DHE was more consistent with INP104 than with Migranal®, with lower variation observed across subjects for both $AUC_{0-inf}$ and $C_{max}$ parameters.

Although bolus intravenous administration of 1 mg DHE mesylate provided greater than 10-fold higher $C_{max}$ than 1.45 mg DHE mesylate administered intranasally by INP104, the high $C_{max}$ achieved with intravenous administration is known to be correlated with adverse events ("AE"s), specifically nausea, and IV DHE mesylate is most commonly administered with an anti-emetic. Within 20-30 minutes following administration, DHE plasma concentrations achieved through INP104 intranasal administration were essentially indistinguishable from concentrations achieved by intravenous administration. Thus, despite a greater than 10-fold higher $C_{max}$, bolus intravenous administration of 1 mg DHE mesylate provided less than 2-fold greater systemic drug delivery, measured as $AUC_{0-inf}$, as compared to INP104 intranasal delivery.

The 8'OH-DHE metabolite of DHE is known to be active, and to contribute to the long-lasting effect of DHE on migraine. We found that intranasal administration of 1.45 mg DHE mesylate by INP104 provides equivalent systemic exposure to the active metabolite of DHE as bolus intravenous administration of 1.0 mg DHE mesylate. In contrast, the 8'-OH DHE metabolite could be detected in only a minority of subjects administered Migranal®.

5.4. Methods of Treating Migraine with or without Aura

Accordingly, in a first aspect, methods are provided for acutely treating migraine headache with or without aura.

The methods comprise administering to a subject with migraine headache an effective dose of a liquid pharmaceutical composition comprising dihydroergotamine (DHE) or a salt thereof, wherein the dose is administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml.

5.4.1. Effective Dose

In various embodiments, the dose is no more than 2.0 mg DHE or salt thereof. In typical embodiments, the dose is less than 2.0 mg DHE or DHE salt.

In certain embodiments, the dose is 1.2-1.8 mg DHE or salt thereof, 1.4-1.6 mg DHE or salt thereof, or 1.4-1.5 mg DHE or salt thereof. In some embodiments, the dose is about 1.2, 1.25, 1.3, 1.35, 1.4, 1.45, 1.5, 1.55, 1.6, 1.65, or 1.7 mg DHE or salt thereof. Ina currently preferred embodiment, the dose is about 1.45 mg DHE or salt thereof.

In some embodiments, the dose is administered as a single undivided dose. In these embodiments, the dose is administered to either the left or right nostril.

In other embodiments, the dose is administered as a plurality of divided doses. In some of these embodiments, the dose is administered as 2, 3, or 4 divided doses. In particular embodiments, the dose is administered as 2 divided doses. In currently preferred embodiments, the dose is administered as 2 divided doses, with one divided dose administered to each nostril.

In embodiments in which the dose is administered as a plurality of divided doses, the entire effective dose is typically administered over no more than 1 minute—that is, all of the plurality of divided doses are administered within 1 minute of administration of the first divided dose. In certain divided dose embodiments, the dose is administered over no more than 45 seconds. In certain divided dose embodiments, the dose is administered over no more than 30 seconds.

In embodiments in which the dose is administered as a plurality of divided doses, the volume of liquid composition administered per divided dose is typically 140-250 µL. In certain embodiments, the volume of liquid composition administered per divided dose is 145 µL-225 µL. In some embodiments, the volume of liquid composition administered per divided dose is 175 µL-225 µL. In particular embodiments, the volume of liquid composition administered per divided dose is about ~180 µL or ~200 µL.

5.4.2. Liquid Pharmaceutical Composition

The liquid pharmaceutical composition comprises dihydroergotamine (DHE) or salt thereof.

In typical embodiments, the liquid pharmaceutical composition comprises a salt of DHE. In preferred embodiments, the liquid composition comprises DHE mesylate.

Dihydroergotamine mesylate—ergotamine hydrogenated in the 9,10 position as the mesylate salt—is known chemically as ergotaman-3', 6', 18-trione, 9,10-dihydro-12'-hydroxy-2'-methyl-5'-(phenylmethyl)-, (5'α)-, monomethanesulfonate. Its molecular weight is 679.80 and its empirical formula is $C_{33}H_{37}N_5O_5 \cdot CH_4O_3S$. The structure is shown in formula (I) below:

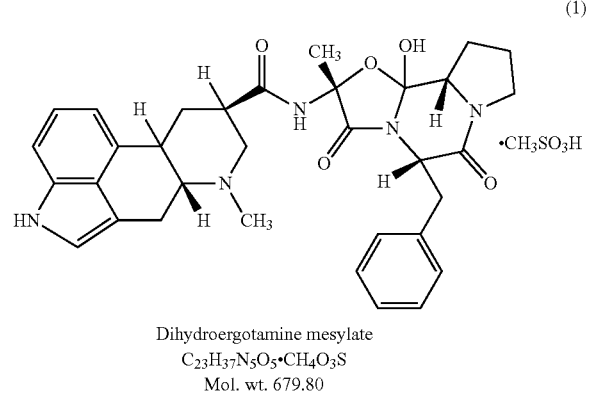

(1)

Dihydroergotamine mesylate
$C_{23}H_{37}N_5O_5 \cdot CH_4O_3S$
Mol. wt. 679.80

In typical embodiments, the liquid pharmaceutical composition comprises DHE mesylate at a concentration of at least 1 mg/ml, 1.5 mg/ml, 2.0 mg/ml, 2.5 mg/ml, 3.0 mg/ml, 3.5 mg/ml, 4.0 mg/ml, 4.5 mg/ml or 5.0 mg/ml. In some embodiments, the liquid pharmaceutical composition comprises DHE mesylate at a concentration of 2.5-7.5 mg/ml. In certain embodiments, the liquid pharmaceutical composition comprises 3.0-5.0 mg/ml or 3.5-6.5 mg/ml DHE mesylate.

In particular embodiments, the liquid pharmaceutical composition comprises 4.0 mg/ml DHE mesylate.

In some embodiments, the composition further comprises caffeine. In particular embodiments, the composition comprises caffeine at a concentration of 1 mg/ml-20 mg/ml, 5 mg/ml-15 mg/ml, or 7.5 mg/ml-12.5 mg/ml. In particular embodiments, the composition comprises 10.0 mg/ml caffeine.

In some embodiments, the composition further comprises dextrose. In certain embodiments, the composition comprises dextrose at a concentration of 5 mg/ml, 10 mg/ml, 15 mg/ml, 20 mg/ml, 25 mg/ml, 30 mg/ml, 35 mg/ml, 40 mg/ml, 45 mg/ml, or 50 mg/ml. In some embodiments, the composition comprises dextrose at a concentration of at least 50 mg/ml.

In various currently preferred embodiments, the liquid pharmaceutical composition comprises 4.0 mg/ml DHE mesylate, 10.0 mg/ml caffeine, and 50 mg/ml dextrose.

5.4.3. Systemic Delivery

The methods comprise administering to a subject with migraine headache an effective dose of a liquid pharmaceutical composition comprising dihydroergotamine (DHE) or a salt thereof, wherein the dose is administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml.

In various embodiments, the mean peak plasma DHE concentration ($C_{max}$) achieved following administration of a dose, whether administered as an undivided dose or a plurality of divided doses, is at least 750 pg/ml, 800 pg/ml, 900 pg/ml, 1000 pg/ml, 1100 pg/ml, or 1200 pg/ml. In some embodiments, the mean DHE $C_{max}$ achieved following administration of a dose is at least 1250, 1300, 1350, 1400, 1450 or 1500 pg/ml. In certain embodiments, the mean DHE $C_{max}$ achieved following administration of a dose is at least 750 pg/ml, 800 pg/ml, 900 pg/ml, 1000 pg/ml, 1100 pg/ml, or 1200 pg/ml. In certain embodiments, the mean DHE $C_{max}$ achieved following administration of a dose is at least 1250, 1300, 1350, 1400, 1450 or 1500 pg/ml. In particular embodiments, the mean DHE $C_{max}$ achieved following administration of a dose is 1000-1500 pg/ml, 1100-1400 pg/ml, or 1200-1300 pg/ml.

In various embodiments, the mean time to $C_{max}$ ($T_{max}$) of DHE following administration is less than 55 minutes. In typical embodiments, the DHE $T_{max}$ is less than 50 minutes, 45 minutes, 40 minutes, or 35 minutes. In some embodiments, the $T_{max}$ of DHE following administration is 30-50 minutes, or 35-45 minutes. In particular embodiments, the DHE $T_{max}$ is no more than 35 minutes, 40 minutes, or 45 minutes.

In various embodiments, the mean plasma $AUC_{0-inf}$ of DHE following administration is at least 3000 pg*hr/ml, 4000 pg*hr/ml, 5000 pg*hr/ml, or 6000 pg*hr/ml. In various embodiments, the mean plasma $AUC_{0-inf}$ of DHE following administration is at least 7000 pg*hr/ml, 8000 pg*hr/ml, 9000 pg*hr/ml, or 10,000 pg*hr/ml. In some embodiments, the mean plasma $AUC_{0-inf}$ of DHE following administration is at least 5000, 5100, 5200, 5300, 5400, 5500, 5600, 5700, 5800, 5900, or 6000 pg*hr/ml. In some embodiments, the mean plasma $AUC_{0-inf}$ of DHE following administration is greater than 6000, 5900, 5800, 5700, 5600, 5500, 5400, 5300, 5200, 5100 or 5000 pg*hr/ml.

In various embodiments, following administration of the dose, the mean peak plasma concentration ($C_{max}$) of 8'-OH- DHE is at least 50 pg/ml. In certain embodiments, the mean $C_{max}$ of 8'-OH-DHE is at least 55 pg/ml.

In various embodiments, following administration of the dose, the mean plasma $AUC_{0-inf}$ of 8'-OH-DHE is at least 500 pg*hr/ml. In some embodiments, the mean plasma $AUC_{0-inf}$ of 8'-OH-DHE is at least 600 pg*hr/ml, 700 pg*hr/ml, 800 pg*hr/ml, 900 pg*hr/ml, or even at least 1000 pg*hr/ml. In certain embodiments, the mean plasma $AUC_{0-inf}$ of 8'-OH-DHE is at least 1100 pg*hr/ml, 1200 pg*hr/ml, 1250 pg*hr/ml, 1300 pg*hr/ml, 1400 pg*hr/ml, or 1500 pg*hr/ml.

5.4.4. Migraine

The methods described herein are used to acutely treat migraine headache, with or without aura.

In various embodiments, the subject has had onset of at least one prodromal symptom of migraine, without onset of headache pain. In certain embodiments, the subject has had onset of at least one prodromal symptom selected from neck stiffness, facial paresthesia, photosensitivity, acoustic sensitivity, and visual aura.

In various embodiments, the subject has had onset of at least one symptom associated with acute migraine. In certain embodiments, the subject has had onset of at least one symptom selected from visual aura; headache pain, including dull, throbbing, or pulsing pain; photosensitivity; acoustic sensitivity; nausea; vomiting. Visual aura and headache pain may be unilateral or bilateral, focal or diffuse.

In various embodiments, administration is performed within 5 minutes, 10 minutes, 15 minutes, or 30 minutes of onset of at least one prodromal symptom. In various embodiments, administration is performed within 5 minutes, 10 minutes, 15 minutes, or 30 minutes of onset of at least one acute symptom.

In typical embodiments, the subject performs the administration (self-administration). In some embodiments, the administration is performed by another individual, such as a parent, guardian, caregiver, or medical professional.

In some embodiments, migraine to be treated is associated with menstruation. In some embodiments, migraine to be treated has proven resistant to triptans.

In various embodiments, the methods are used for acute treatment of cluster headaches rather than migraine.

5.4.5. Device

In the methods described herein, the dose is administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml.

5.4.5.1. Compound Delivery Device

In various embodiments, the intranasal administration device is a "compound delivery device" as described in U.S. Pat. No. 9,550,036, the disclosure of which is incorporated herein by reference in its entirety.

5.4.5.2. Medical Unit Dose Container Device

In various embodiments, the intranasal administration device is a "medical unit dose container" device as described in WO 2014/179228, the disclosure of which is incorporated herein by reference in its entirety.

5.4.5.3. Manually Activated, Propellant-Driven, Metered-Dose Device

In typical embodiments, the intranasal delivery device is a manually actuated, propellant-driven, metered-dose intranasal administration device.

In currently preferred embodiments, the liquid pharmaceutical composition and propellant are not in contact within the device prior to first manual actuation, and, optionally, not in contact within the device between successive manual actuations. In such embodiments, the device typically comprises a vial and a canister, wherein the liquid pharmaceutical composition is contained in the vial and the propellant is contained in the canister. Typically, the canister is a pressurized canister of propellant. In typical embodiments, the propellant is a hydrofluoroalkane propellant suitable for pharmaceutical use. In specific embodiments, the propellant is hydrofluoroalkane-134a.

In various embodiments, each manual actuation brings a metered volume of liquid pharmaceutical composition and a separately metered volume of propellant into contact within a dose chamber of the device. Contact of propellant with liquid pharmaceutical composition within the dose chamber of the device propels the dose towards the nozzle of the device, creating a spray as the dose is expelled through the nozzle of the device. In particularly preferred embodiments, the nozzle has a plurality of lumens, and the spray is ejected simultaneously through a plurality of nozzle lumens.

As discussed in further detail below with respect to kits, in some embodiments the vial is nonintegral to the device and is configured to be attachable thereto. In particularembodiments, the vial is configured to be threadably attachable to the device.

5.4.5.3.1. In-Line Nasal Delivery Device

In certain currently preferred embodiments, the manually actuated, propellant-driven metered-dose intranasal administration device is an "in-line nasal delivery device" as described in WO 2017/044897, the disclosure of which is incorporated herein by reference in its entirety.

Typically, in these embodiments the device delivers at least a portion of the dose of liquid pharmaceutical composition to the nasal cavity beyond the nasal valve, including delivery to the turbinates and/or the olfactory region. In certain embodiments, the device delivers at least 25%, 30%, 40%, 50%, 60%, or 70% of the dose of liquid pharmaceutical composition beyond the nasal valve. In certain embodiments, the device delivers liquid pharmaceutical composition so that at least 25%, 30%, 40%, 50%, 60%, or 70% of the dose of liquid pharmaceutical composition is brought into contact with the upper third of the nasal cavity (nasal epithelium) of the subject.

Figure 1:
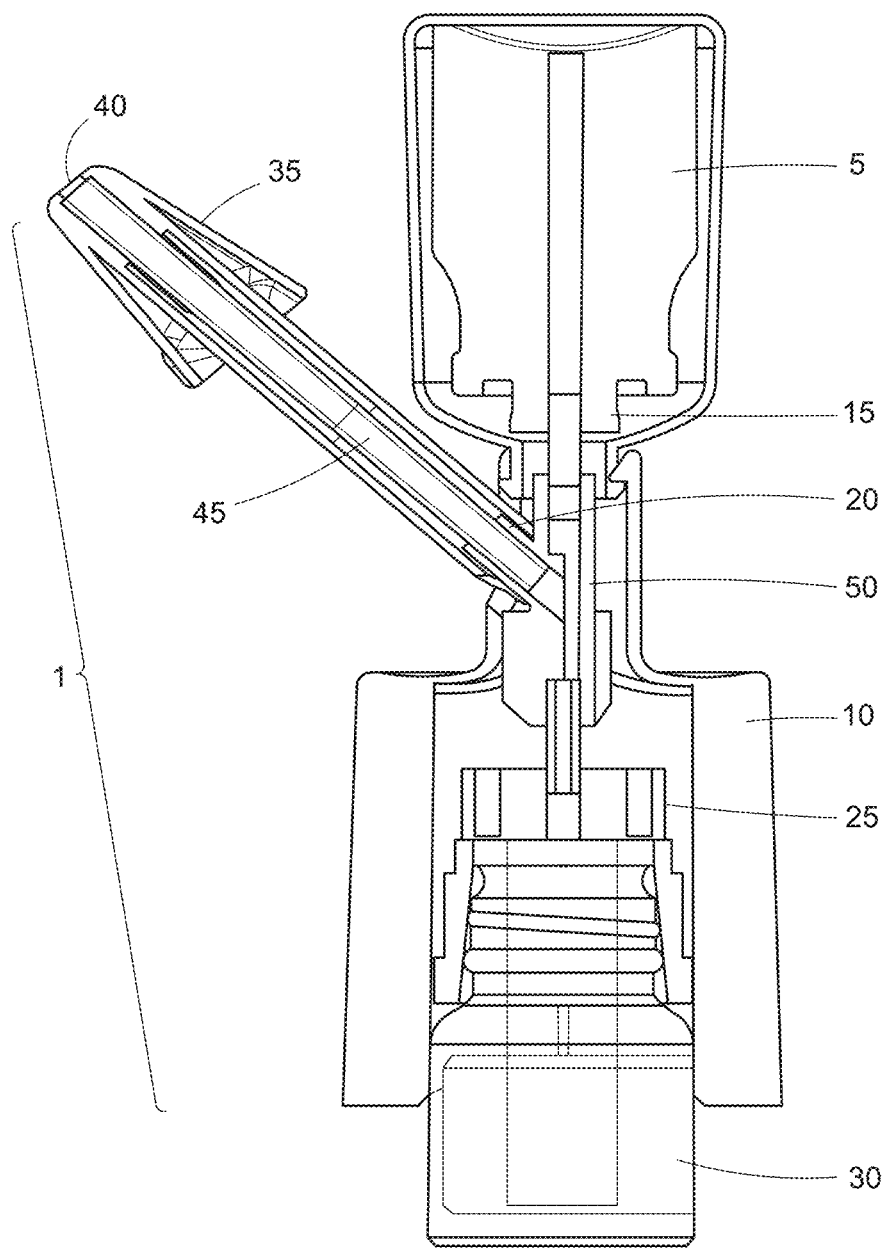
FIG. 1 shows a cross section of an embodiment of a handheld, manually actuated, metered-dose, propellant-driven intranasal administration device useful for precision olfactory delivery of dihydroergotamine (DHE).

As shown in FIG. 1, the in-line nasal delivery device 1 includes a housing 10, diffuser 20, tip 35, nozzle 40, dose chamber 45, an actuator 50, and a pump 25 to move the liquid pharmaceutical composition into the dose chamber 45. In one series of embodiments, the in-line nasal device 1 is associated and cooperative with a propellant canister 5, a propellant valve 15, and a vial 30 of liquid pharmaceutical composition cooperative with the pump 25 to move the liquid pharmaceutical composition into the dose chamber 45.

In one series of embodiments, the diffuser 20 is a frit 21 (not shown in FIG. 1). The diffuser provides for the conversion of the liquefied propellant in the propellant canister 5 to gas and/or an increase in temperature of the propellant.

In one series of embodiments, the propellant valve 15 is a metered dose propellant valve 16.

In one series of embodiments, the liquid pharmaceutical composition is supplied in the form of a sealed vial 30, e.g., of glass. In one series of embodiments, the vial 30 has a neck 31 (not shown) that is sealed by a removable closure 32 (not shown), for example but not limited to sealed with a plastic cover, crimped metal seal, and rubber stopper (for stability and sterility purposes). When the closure 32 is removed, the device 1 can be engaged with the vial 30. In one series of embodiments, device 1 can be engaged with vial 30 by cooperation with the neck 31 of the vial 30. In a related aspect, further discussed below, sealed vial 30 and device 1 can be co-packaged into a kit to be assembled at time of use.

In certain embodiments, vial 30 is a 3.5-mL amber glass vial.

A pump 25 moves the liquid pharmaceutical composition into the dose chamber 45.

The propellant canister 5 is a canister of a compressed gas or a liquefied propellant. Compressed gases include but are not limited to compressed air and compressed hydrocarbons. In one series of embodiments, the compressed gas is nitrogen or carbon dioxide. Liquefied propellants include but are not limited to chlorofluorocarbons and hydrofluoroalkanes. In a preferred embodiment, propellant canister 5 contains HFA-134a.

The canister 5 will generally be provided with a propellant valve 15 by which the gas flow can be controlled.

The tip 35 includes a nozzle 40. In one series of embodiments, the nozzle 40 has a plurality of nozzle openings 41 (not shown) (synonymously, nozzle lumens). Through the plurality of nozzle openings 41, the liquid pharmaceutical composition and propellant is delivered to the nasal cavity.

Figure 2:
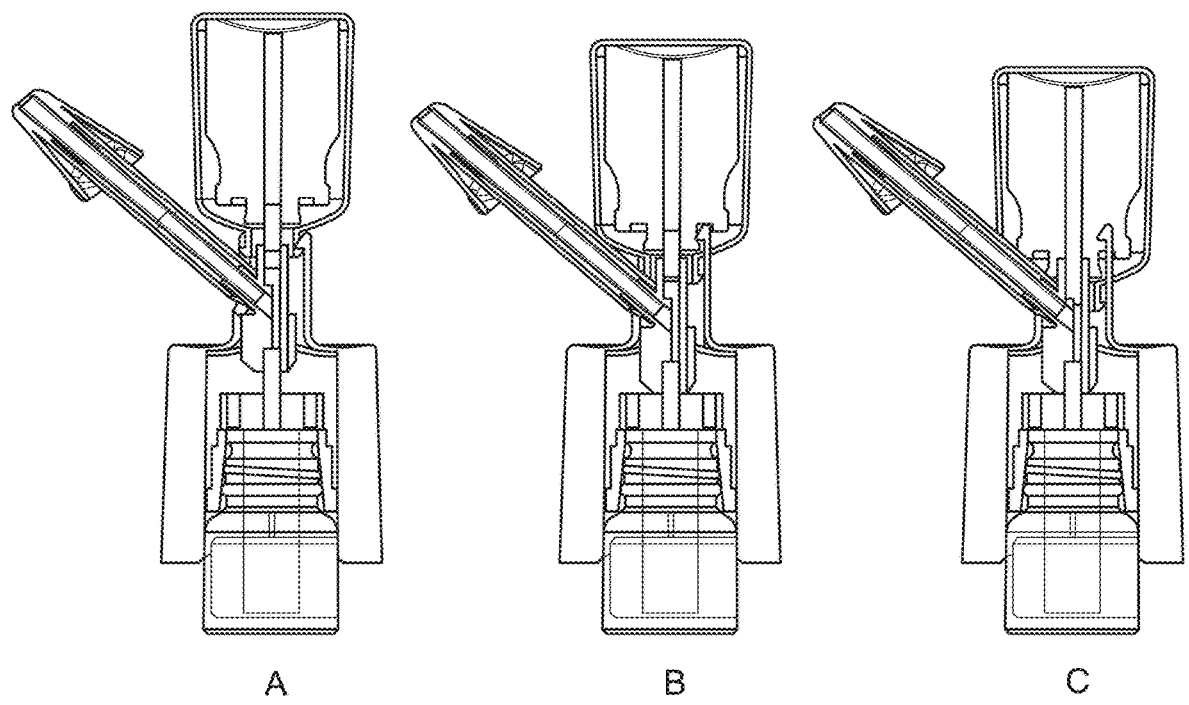
FIG. 2 shows a cross section of the in-line nasal delivery device of FIG. 1 in the stages of rest and actuation.

Actuation of the propellant canister 5 is effectively coordinated with actuation of the pump 25 for the vial 30 for the liquid pharmaceutical composition. The arrangement may be such that actuation of the vial 30 for the liquid pharmaceutical composition causes actuation of the propellant canister 5. FIG. 2 shows the device 1 at rest (FIG. 2A) and in actuation (FIG. 2B and 2C).

As an example, the staging of the device 1 actuation is as follows. The housing 10 is compressed to prime the propellant canister 5. When the housing 10 is compressed, an actuator 50 remains stationary in the housing 10 while the propellant canister 5 and the vial 30 move towards the actuator 50. At this time, the propellant valve 15 associated with the propellant canister 5 is not actuated by compression. The actuator 50 acts upon the pump 25 compressing the pump 25 and the liquid pharmaceutical composition from the vial 30 is moved into the dose chamber 45. After a majority of the liquid pharmaceutical composition has moved into the dose chamber 45, the actuator 50 acts upon the propellant valve 15 and the propellant valve 15 begins to compress. The continued depression of the actuator 50 releases the propellant from the propellant canister 5. The propellant pushes the liquid pharmaceutical composition as it exits the device 1 through the nozzle openings (lumens) 41 (not shown) of the nozzle 40 located in the tip 35. The actuator 50 provides for first actuation of the pump 25, then once the pump 25 bottoms out, the continued depression of the actuator 50 provides for release of the propellant from the canister 5.

In an alternative implementation of the device 1 (not shown), the device 1 does not include a diffuser 20. In such embodiments, the device typically incorporates another type of dose retaining valve.

Figure 3:
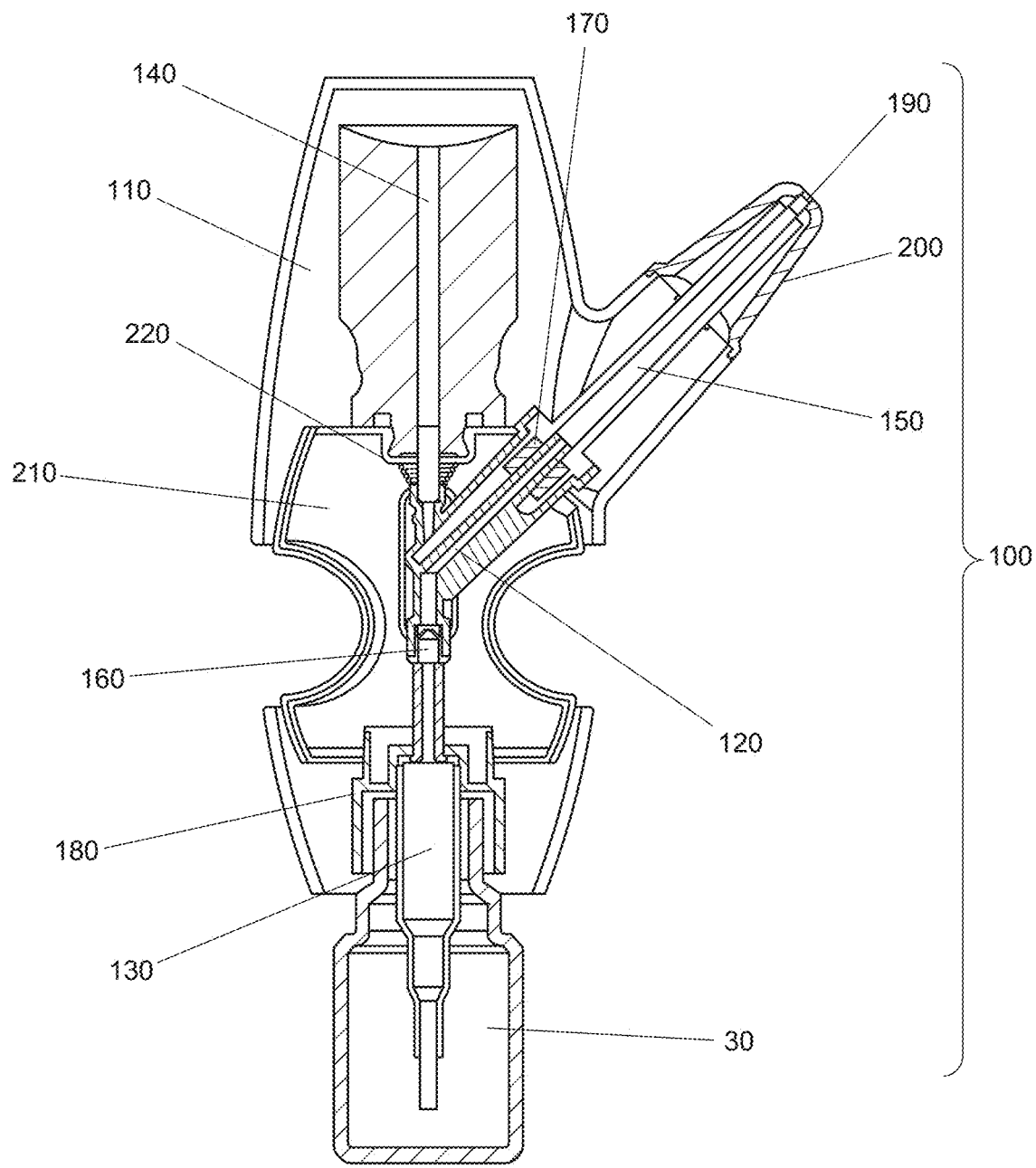
FIG. 3 shows a cross section of another implementation of the in-line nasal delivery device.

FIG. 3 shows yet another implementation of the device 100. The device 100 can deliver a single or multiple dose from a vial 30 or other container. The device 100 allows for multiple doses to be delivered from the vial 30, or a single dose. For example, the vial 30 may contain a volume of liquid pharmaceutical composition for multiple doses, while the user may decide to only deliver a single dose from the vial 30. The liquid pharmaceutical composition may be a drug, active pharmaceutical ingredient, or a pharmaceutical formulation.

Initially, the vial 30 may be separate from the rest of the assembled device 100. At the time of use, the device 100 and vial 30 are taken out of their respective packaging. Prior to use, the vial 30 will generally be sealed. In the embodiment where the vial 30 is covered by a plastic cover, metal seal and stopper, the plastic cover and metal seal are pulled away from the top of the vial 30, and the rubber stopper is removed from the vial 30. The vial 30 may be screwed into a pump fitment 180 located at the base of the device 100. For example, but not limitation, the vial 30 may have female threads which can be screwed into male threads on a pump fitment 180, or vice versa. The vial 30 may contain, for example but not limited to, inclusive of end points, 2-3 ml, in another embodiment 2-2.5 ml of liquid pharmaceutical composition.

As shown in FIG. 3, the device 100 includes a housing 110. The housing 110 contains components of the device 100 including the Y-junction 120. The Y-junction 120 has three branches radiating from a common base. The Y-junction and its three branches may be a molded component. The Y-junction 120 establishes both fluid and gas paths within the device 100, and connects the metered dose pump 130, the dose chamber 150, and the propellant canister 140 when the propellant canister 140 is assembled with the device.

As shown in FIG. 3, for use of the device 100, the user will generally orient the device 100 with the propellant canister 140 assembled and located at the top and the vial 30 assembled and located at the bottom. Housed within the device's 100 housing 110, the optional check-valve 160 (attached to the metered dose pump 130 stem) press fits into a receiving hub of a first branch of the Y-junction 120. An internal bore provides fluid communication from the metered dose pump 130, through the optional check-valve 160 and to a third branch of the Y-junction 120, which connects to the dose chamber 150. In one series of embodiments, the check valve 160 is an elastomeric component that installs within a plastic housing between the metered dose pump 130 and the Y-junction 120. The optional check valve 160: (a) reduces or eliminates dose leakage which could occur through the metered dose pump 130 if the pump stem was depressed and the propellant canister 140 was actuated; (b) allows for improved consistency in dose delivery by the device 100; and/or provides that liquid pharmaceutical composition is not pushed back down the internal dose loading channel 230 of the Y-junction 120 and into the metered dose pump 130.

When oriented as to be used in operation, housed within the device's 100 housing 110, towards the top of the device 100, the propellant canister 140 press fits into a second branch of the Y-junction 120, establishing the gas path through internal bores, through the diffuser 170 and to the dose chamber 150.

Figure 4:
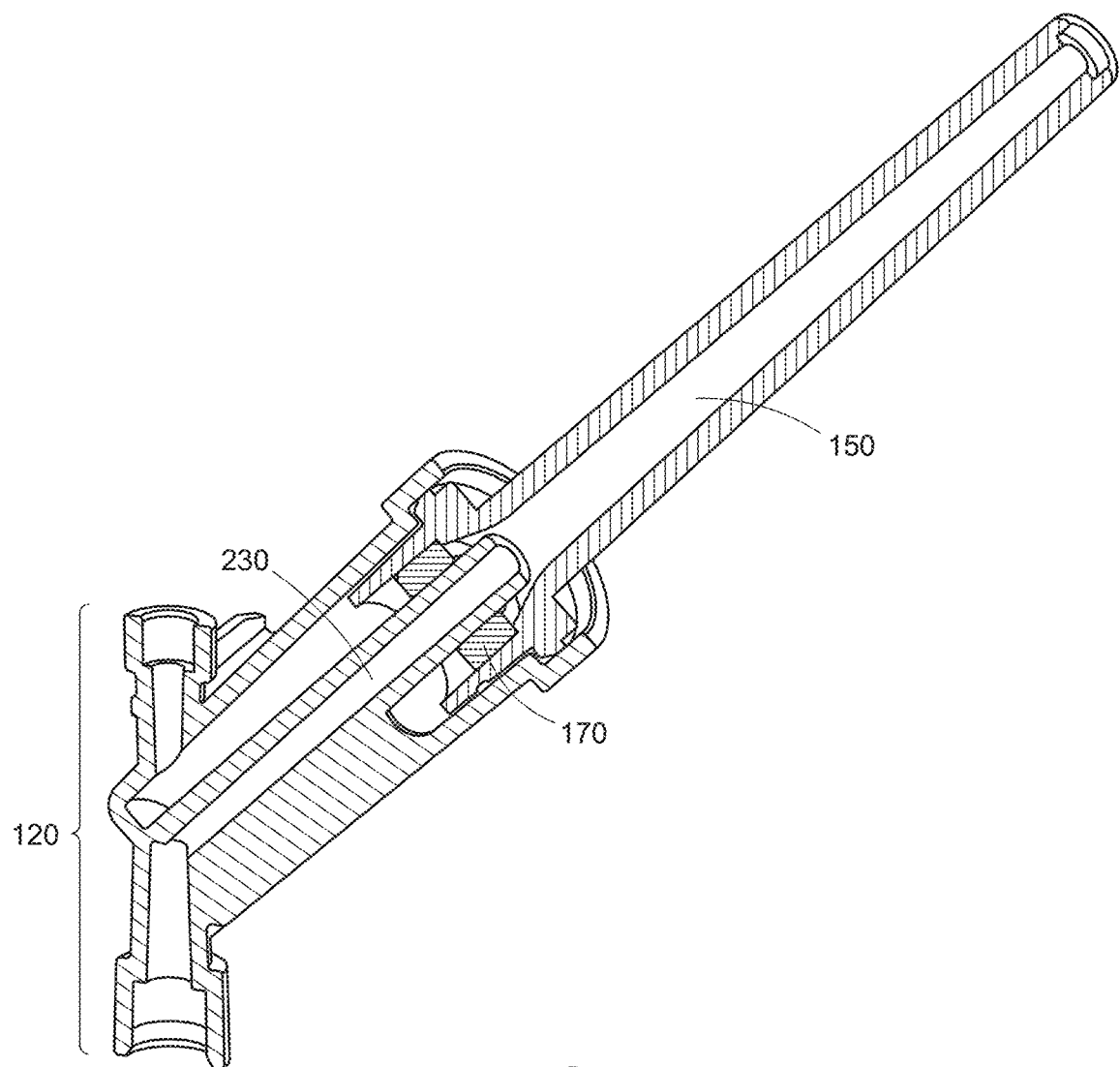
FIG. 4 shows a cross section of the diffuser as seated within the device.

In this implementation of the device 100, the diffuser 170 is annular. As shown in FIG. 4, the annular diffuser 170 sits inside a bore on the back end of the dose chamber 150. The external diameter of the annular diffuser 170 is in a compression fit with the dose chamber 150. In other embodiments, not shown, the annular diffuser is fixed to the dose chamber using means other to or in addition to compression fit.

An internal dose loading channel 230 which is molded as a portion of the Y-junction 120 fits into the inner bore of the annual diffuser 170 when the dose chamber 150 is installed onto the Y-junction 120. The inner diameter of the annular diffuser 170 is in compression with the internal dose loading channel 230 portion of the Y-junction 120. The annular diffuser 170 is seated between the outer wall of the internal dose loading channel 230 and the inner wall of the dose chamber 150, sealing against both of those surfaces to form the bottom of the dose chamber 150. Additional embodiments of the diffuser 170, dose chamber 150, and Y-junction 120 are discussed with regards to FIGS. 12-13.

In one series of embodiments, the diffuser 170 is a frit 171 (not shown). In other embodiments, the diffuser 170 is a component that is homogenously or heterogeneously porous. In some embodiments, the diffuser 170 may be a disk-shaped member. The diffuser 170: (a) provides for the conversion of the liquefied propellant in the propellant canister 140 to gas; (b) provides an increase in temperature of the propellant; (c) acts to prevent the propellant from flowing back into the device 100; (d) acts to prevent the liquid pharmaceutical composition from flowing back into the device 100; and/or (e) acts to allows gas flow into the dose chamber 150 while preventing the liquid pharmaceutical composition from leaking out. The diffuser may be made of a porous polymer material.

Figure 6:
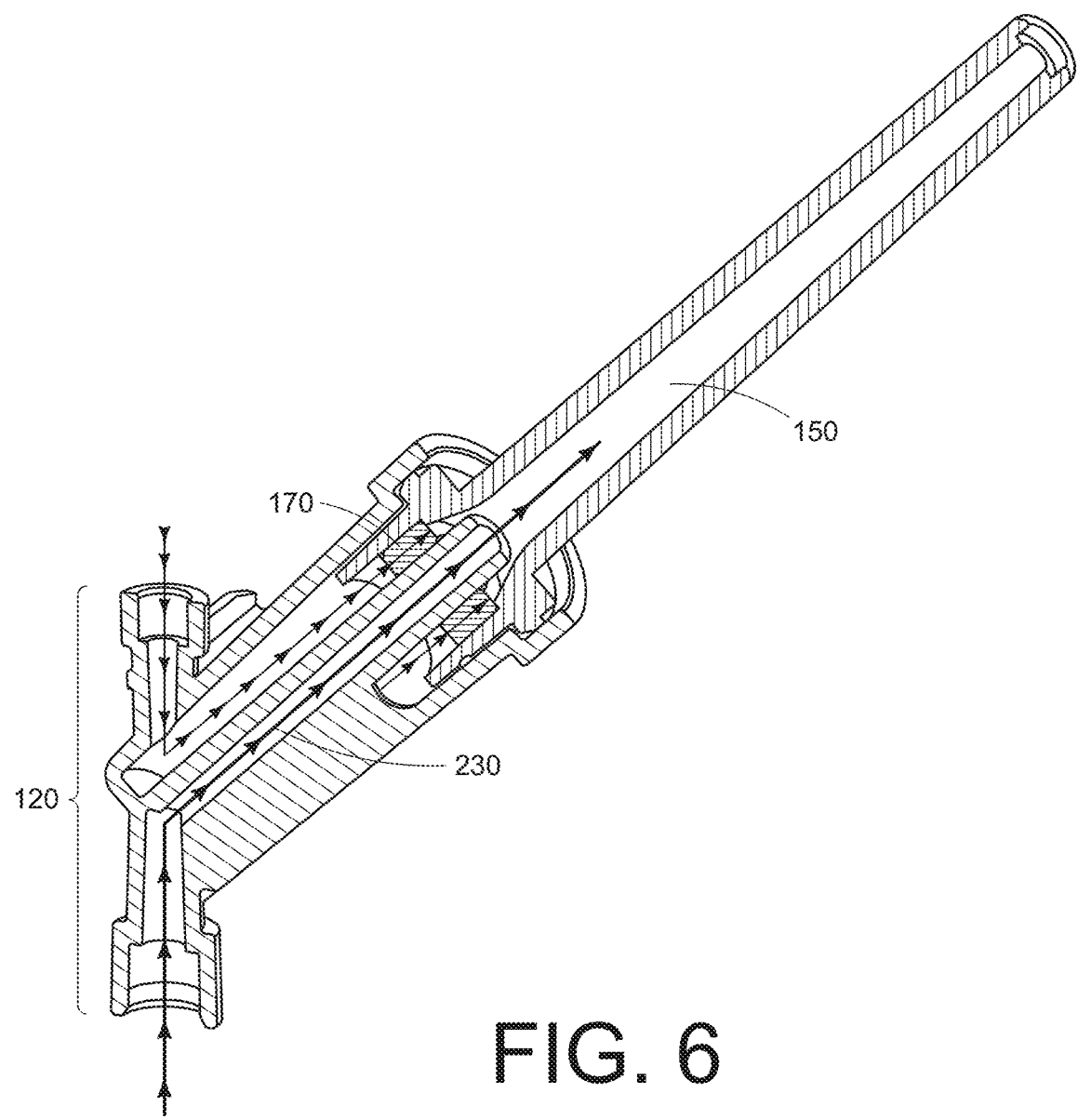
FIG. 6 shows arrows representing both dose and propellant flow.

The relationship in operation of the device 100 between the liquid pharmaceutical composition, the diffuser 170, the inner dose loading tube 230, the dose chamber 150 and the Y-junction 120 are shown at least in FIG. 6. In operation, the liquid pharmaceutical composition being loaded into the dose chamber 150 takes the less restrictive route, flowing out of the vial 30 and filling the dose chamber 150 rather than loading backwards through the diffuser 170 and into the delivery path of the propellant of the Y-junction 120. In operation of the device 100, the staging of operation and the amount of time required for operation of the device allows the diffuser 170 to restrict liquid pharmaceutical composition from flowing back into the Y-junction 120 for the period of time needed, as the propellant canister 140 is activated after liquid pharmaceutical composition loading. During proper device 100 use, the entire actuation of the device 100, including metered dose pump 130 and propellant canister 140, is approximately a second or less than a second. The loaded dose in the dose chamber 150 does not have enough time to flow backwards into the Y-junction 120. Immediately after the dose chamber 150 is full, the propellant expels the liquid pharmaceutical composition from the device 100.

On the third leg of the Y-junction 120 at a 45-degree angle, the dose chamber 150 press fits into the Y-junction 120, completing the flow paths for both gas and fluid through the device. In one series of embodiments, the angle is 30 degrees, 35 degrees, 40 degrees, 45 degrees, 50 degrees, 55 degrees, 60 degrees, inclusive of endpoints and intervening degrees.

The Y-junction 120 may contain engagement ribs (not shown) to help secure and position the assembly within the housing 110 of the device 100.

The device 100 includes a pump fitment 180. The pump fitment 180 secures the metered dose pump 130 to the vial 30 and holds both components in place during device 100 use. One series of embodiments of the pump fitment 180 is that it consists of engagement ribs that retain it within the housing 110, provide vertical displacement, and prevent rotation during installation of the vial 30.

Figure 5A:
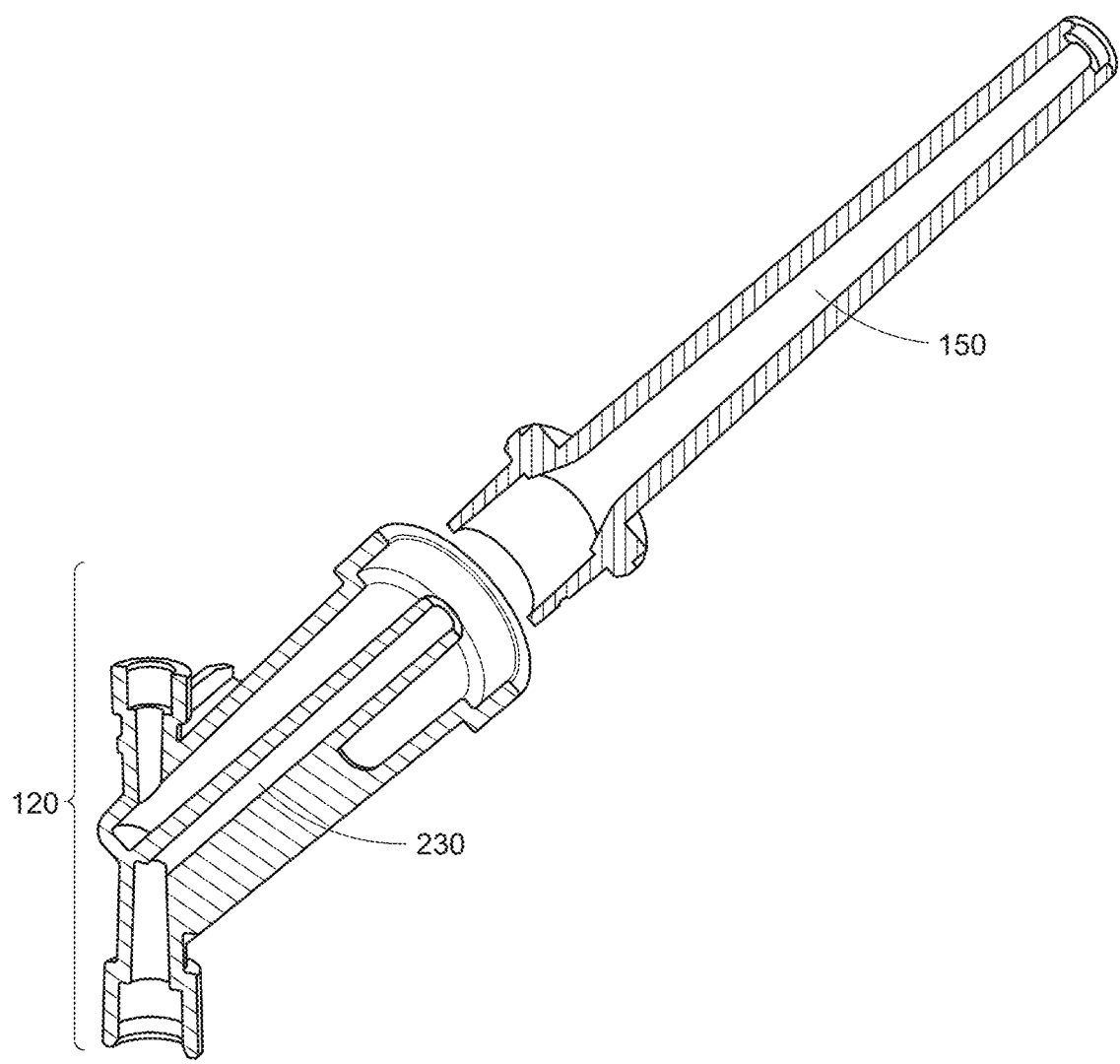
FIG. 5A shows an exploded view of the dose chamber and the Y-junction unassembled.
Figure 5B:
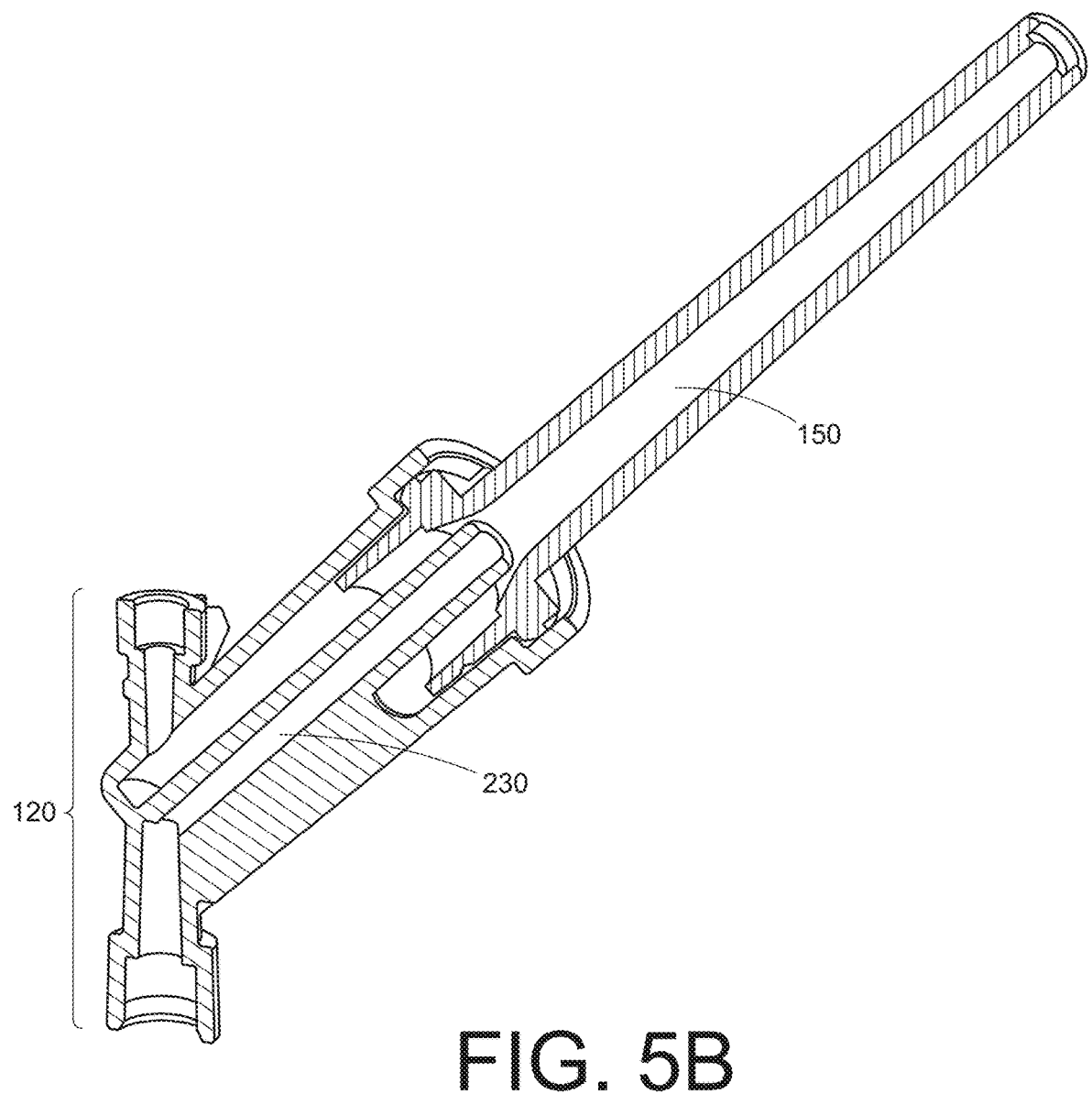
FIG. 5B shows an exploded view of the dose chamber and Y-junction in cooperation.

The device 100 includes a dose chamber 150. The dose chamber 150 receives and stores the liquid pharmaceutical composition that has been pushed out of the inner tube of the Y-junction 120. When the propellant canister 140 is actuated, the Y-junction 120 and dose chamber 150 are pressurized and the propellant gas expels the liquid pharmaceutical composition out of the dose chamber 150. As shown in FIGS. 5A and 5B, the dose chamber 150 is press fit into the Y-junction 120. The nozzle 190 is installed into the end of the dose chamber 150 opposite where it is press fit into the Y-junction 120.

The nozzle 190 is installed into the distal end (end opposite where the dose chamber 150 is press fit into the Y-junction 120) of the dose chamber 150, forming a liquid and gas-tight seal around the outer diameter. During actuation of the device 100, propellant evacuates liquid pharmaceutical composition from the dose chamber 150, pushing it out the nozzle 190.

The nozzle 190 forms the narrow plume angle (for example, an angle of 1 to 40 degrees, including endpoints and angles intermittent there between; in one series of embodiments the angle is 5 degrees, 10 degrees, 15 degrees, 20 degrees, 25 degrees, 30 degrees, 35 degrees) multi-stream deposition. The nozzle 190 and resultant angle of the plume produced promotes delivery of the liquid pharmaceutical composition to the olfactory region of the user's nasal cavity.

Figure 8:
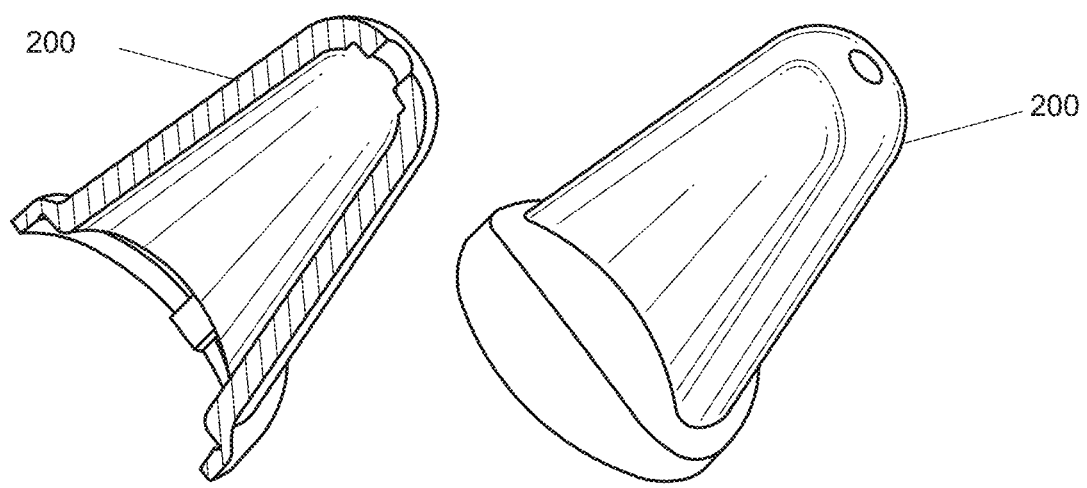
FIG. 8 shows a cross section of the optional nose cone and a side elevation of the optional nose cone.

In this implementation, as shown in FIG. 8, the device 100 may include an optional nose cone 200. The external geometries of the nose cone 200 assist in providing proper alignment of the device 100 during insertion into the nose. The diametrically opposed flat sides aid with placement against the septum of either naris, with the depth stop providing correct depth of insertion. The nose cone 200 adds redundancy to nozzle 190 retention through mechanical interference incorporated into the design. As shown in FIG. 3 and FIG. 8, there is an opening in the nose cone 200 which aligns with the nozzle 190. The nose cone 200 is not part of the pressurized flow path.

The housing 110 represents the body of the device 100. The housing 110 includes two different "clamshells" concealing the components of the device 100 and retaining all components to ensure functionality. The housing 110 houses the metered dose pump 130 and pump fitment 180, the actuator grip 210, the Y-junction 120, the propellant canister 140, and the dose chamber 150. The nose cone 200 engages onto the outer geometry of the housing 110, or may be optionally integrated into the design of the clamshells. An additional embodiment of the nose cone 200 is discussed with regards to FIG. 14. The housing 110 is designed to assemble easily through the use of, for example but not limited to, mattel pins, snaps, post or screws, or a combination thereof, molded into the geometry.

Figure 7:
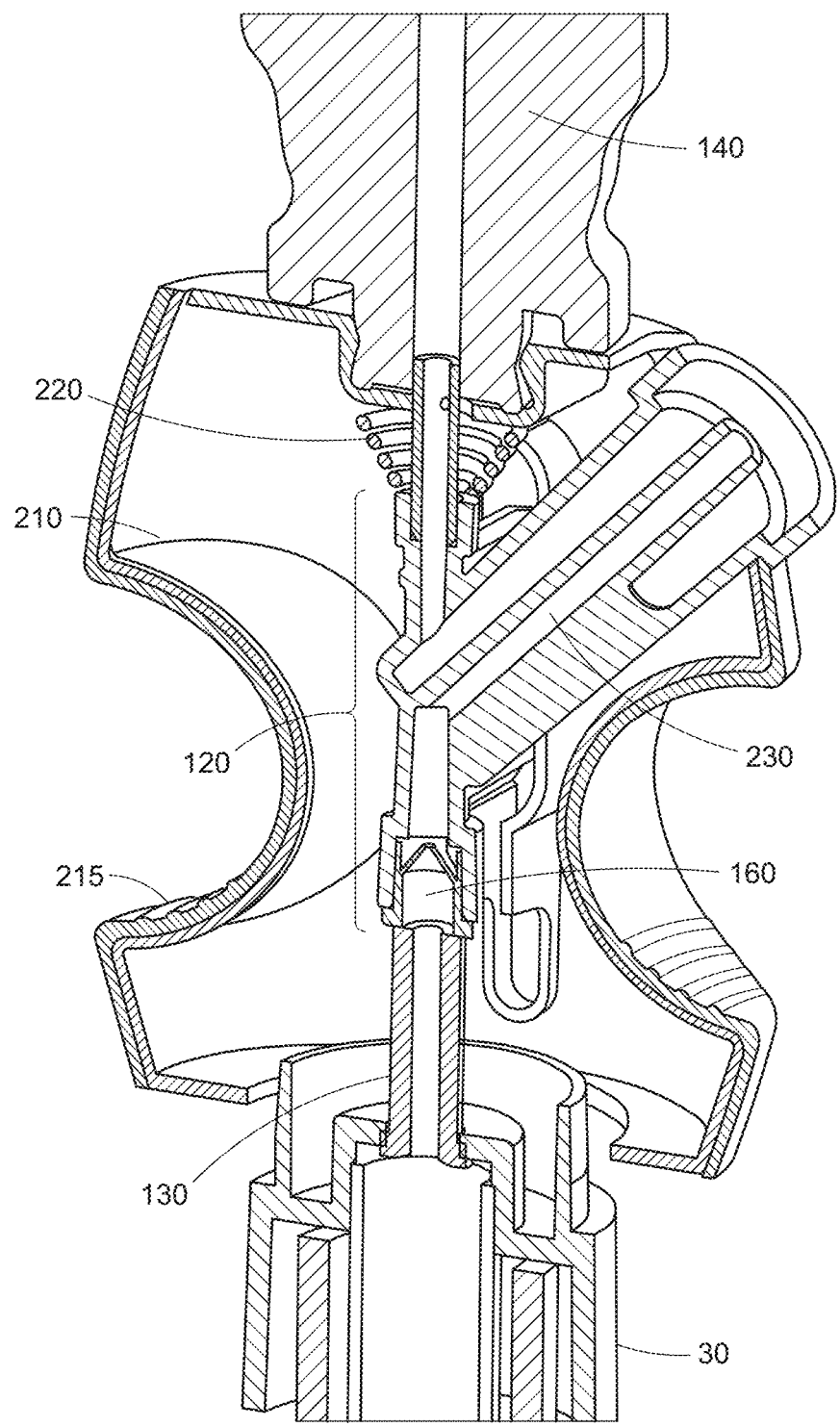
FIG. 7 shows the actuator grip and conical spring arrangement.

The actuator grip 210 provides for actuation displacement by the user. The actuator grip 210 is composed of two parts, actuator grip A and actuator grip B and surround the Y-junction 120 and reside within the housing 110. FIG. 7 shows two finger grip notches 215 are designed into the actuator grip 210 to allow the user to engage the device 100 with the fingers, for example but not limited to, the index and middle finger. These finger grip notches 215 allow the user to apply downward movement leading to device 100 actuation.

The metered dose pump 130 draws liquid pharmaceutical composition up from the vial 30 to the Y-junction 120. The metered dose pump 130 may utilize a custom pump fitment 180 to promote functionality within the device 100, and allow attachment of the vial 30 via threads. The metered dose pump 130 may deliver, for example but not limited to, volumes of 130 µl, 140 µl, 150 µl, 160 µl, 170 µl, 180 µl, 190 µl, 200 µl, or 230 µl during actuation. Commercially available metered dose pumps 130 can be used.

For the device 100 to consistently deliver liquid pharmaceutical composition, the metered dose pump 130 must first deliver liquid pharmaceutical composition, followed by propellant canister 140 actuation to expel the liquid pharmaceutical composition. As shown in FIG. 7, one manner in which to accomplish this is via a conical spring 220 between the propellant canister 140 and Y-junction 120 to create the necessary propellant canister 140 actuation force resulting in the correct order of actuation between the metered dose pump 130 and propellant canister 140. In one implementation, a conical spring 220 is used, although this force is not limited to being produced by a conical spring 220 as other mechanisms can be used. In one series of embodiments, the conical spring 220 has a near zero preload, with a k value of about 25.5 lbf in and a maximum load of 3.2 lbf. Selection of the spring or mechanism will include the considerations of: (a) providing for proper device 100 staging; (b) physical space in the device 100; and/or (c) and user feedback regarding how stiff of a conical spring 220 still allows a variety of users to activate the device 100.

The conical spring 220 is installed inline between the propellant canister 140 and Y-junction 120. The actuator grip 210 physically holds the propellant canister 140. The user activates the device 100 by, for example, applying an in-line force acting down from the actuator grips 210, and up from the vial 30. This force simultaneously acts to activate both the metered dose pump 130 and the propellant canister 140. The conical spring 220 acts in parallel to the internal propellant canister metering valve spring, increasing the necessary force required to activate the propellant canister 140. By choosing the conical spring 220 such that the necessary force required to actuate the propellant canister 140 is in excess of the maximum necessary force required to completely actuate the metered dose pump 130, the device 100 provides that dose is loaded into the dose chamber 150 before propellant gas begins to expel liquid pharmaceutical composition from the device 100.

In another embodiment, an extension spring is used in lieu of a conical spring. The extension spring is discussed with regards to FIG. 12A.

During device 100 actuation, the metered dose pump 130 draws liquid pharmaceutical composition up from the vial 30 at the bottom of the device 100 via the Y-junction 120, through the internal dose loading channel 230 and into the dose chamber 150. The internal dose loading channel 230 provides a clear route for the liquid pharmaceutical composition to be loaded ahead of the diffuser 170, without needed to physically pass through the porous material of the diffuser 170. As shown in FIG. 6, small arrow heads represent the flow of the propellant while large arrow heads represent the flow of the liquid pharmaceutical composition. Priming shots may be required to completely fill the metered dose pump 130 and internal dose loading channel 230 of the Y-junction 120 prior to user dosing. An optional dose cap (not shown) may cover the nose cone 200 of the device 100 and captures the priming shots while also providing a means of visual indication to the user that the device is primed.

In the second stage of device 100 actuation, once the dose chamber 150 has been filled, the propellant canister 140 releases propellant which enters through the top of the Y-junction 120, following the path shown by smaller arrow heads in FIG. 6. The propellant flows physically through the porous material of the diffuser 170, which promotes the vaporization of the propellant. The diffuser 170 and the path along which the propellant travels (shown by the arrow heads in FIG. 6) convert liquid propellant into gas propellant, resulting in expansion and propulsion of the propellant. The propellant first contacts the liquid pharmaceutical composition at the proximal (distal being closer to the nozzle 190, proximal being farther away from the nozzle 190) face of the diffuser 170 as seated in the device 100. As the propellant continues to expand, it pushes the liquid pharmaceutical composition forward (toward the nozzle 190) in the dose chamber 150, exiting though the nozzle 190 at the end of the dose chamber 150.

The propellant canister 140 provides the propulsive energy for the device 100. The stem of the propellant valve seats into the top receiver of the Y-junction 120. During use, the user presses down on the actuator grips 210 which pulls the propellant canister 140 body down, actuating the propellant valve. This releases a metered volume of liquid propellant. As the propellant vaporizes and expands, the liquid pharmaceutical composition is forced toward the distal end of dose chamber 150 and out through the nozzle 190.

As a non-limiting example of propellant, the propellant canister 140 uses HFA 134A as the propellant for the system. Other propellants are envisioned. There are commercially available propellant canisters 140.

In certain embodiments, the device, propellant canister, and vial containing liquid pharmaceutical composition are provided separately, optionally co-packaged into a kit, and thereafter assembled for use. In certain embodiments, propellant canister 140 is provided assembled within device 100 and the vial containing liquid pharmaceutical composition is provided separately, optionally with the device (with integrated canister) and vial co-packaged into a kit. In some embodiments, the device, propellant canister, and vial containing liquid pharmaceutical composition are provided to the user fully assembled.

5.4.5.3.2. Alternate In-Line Nasal Delivery Device

Figure 9A:
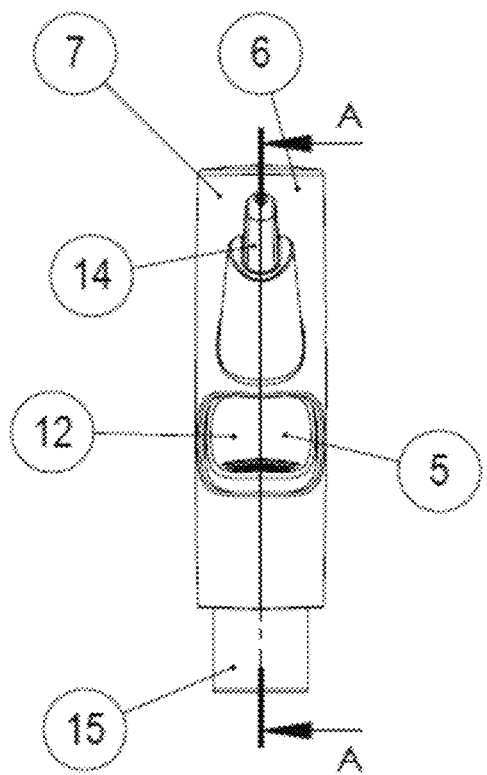
FIGS. 9A and 9B illustrate the device used in the phase I clinical trial described in Example 2, with further description of the numbered parts set forth in Table 1.
Figure 9B:
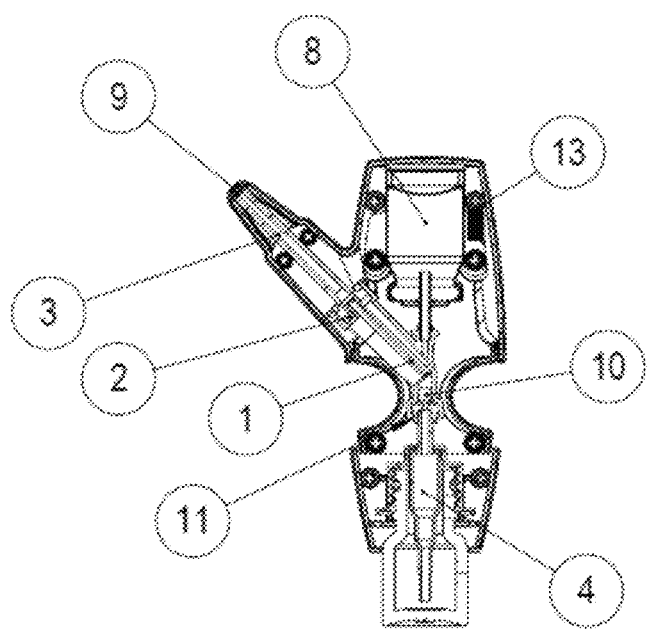

In certain embodiments, the device comprises the following parts; part numbering is as depicted in FIGS. 9A and 9B.

TABLE 1

Clinical Trial Device

| COMPONENT | PART ID | PART NAME | MATERIAL |
|---|---|---|---|
| Device | 1 | Y-Junction | PP |
| | 2 | Diffuser | PE |
| | 3 | Dose Chamber | PP |
| | 4 | Metering Pump | POM; PE Medium Density; Chlorobutyl Rubber PP; White Masterbatch Colorant Stainless Steel; PE (HDPE + LDPE) |
| | 5 | Finger Grip (right) | ABS |
| | 6 | Clamshell (right) | ABS |
| | 7 | Clamshell (left) | ABS |
| | 8 | Propellant Canister | Propellant: HFA Canister: Anodized Aluminum HFA Metering Valve: Anodized Aluminum; Polyester; Stainless Steel; EF327 Seat and Gasket |
| | 9 | Nozzle | LCP |
| | 10 | Check Valve | Silicone |
| | 11 | Check Valve Adapter | PP |
| | 12 | Finger Grip (left) | ABS |
| | 13 | Extension Spring | Stainless Steel |
| | 14 | Nose Cone | ABS |
| Drug | 15 | Drug Vial | 3.5 ml amber glass vial container |

Abbreviations
ABS = acrylonitrile butadiene styrene;
CMO = contract manufacturing organization;
HDPE = high density polyethylene;
HFA = hydrofluoroalkane-134a;
LCP = liquid crystal polymer;
LDPE = low density polyethylene;
PE = polyethylene;
POM = polyacetal copolymer;
PP = polypropylene The vial contains liquid pharmaceutical composition in an amount sufficient for at least one total dose of DHE, or salt thereof, to be delivered by the device, in a single undivided or a plurality of divided doses. In particular embodiments, the vial contains liquid pharmaceutical composition in an amount sufficient for at most one total dose of DHE, or salt thereof, to be delivered by the device, in a single undivided or a plurality of divided doses.

In various embodiments, the propellant canister contains pressurized propellant in an amount sufficient for optional priming of the device followed by delivery of at least one total dose of DHE, or salt thereof, to be delivered by the device, in a single undivided or a plurality of divided doses. In particular embodiments, the propellant canister contains pressurized propellant in an amount sufficient for optional priming of the device followed by delivery of at most one total dose of DHE, or salt thereof, to be delivered by the device, in a single undivided or a plurality of divided doses.

In some embodiments, with each actuation, a minority of the pressurized liquid hydrofluoroalkane is converted to gaseous hydrofluoroalkane. In certain embodiments, the quantity of pressurized liquid hydrofluoroalkane is sufficient to permit a predetermined number of device actuations. In some of these embodiments, the quantity is sufficient to permit 2, 3, 4, 5, 6, 7 or 8 actuations. In some embodiments, the quantity is sufficient to permit 10, 11, 12, 13, 14, 15, or even 20 actuations. In certain embodiments, a majority of the pressurized liquid hydrofluoroalkane is converted to gaseous hydrofluoroalkanes after 2, 3, 4, 5, 6, 7, or 8 actuations. In certain embodiments, a majority of the pressurized liquid hydrofluoroalkane is converted to gaseous hydrofluoroalkanes after 10, 11, 12, 13, 14, 15, or 20 actuations.

5.4.5.3.3. Alternate In-Line Nasal Delivery Device

FIG. 12A shows a cross section of an alternate implementation of the in-line nasal delivery device 1200. The in-line nasal delivery device 1200 may be an embodiment of the in-line nasal delivery device 100. For example, the device 1200 may use the same or similar components as the device 100, as described with regards to FIGS. 3-9. Additionally, components of device 1200 and device 100 may be used interchangeably or in some combination thereof. In the embodiment of FIG. 12A, the device 1200 includes a housing 12110, a Y-junction 12120, a metered dose pump 12130, a propellant canister 12140, a dose chamber 12150 (shown in FIG. 13A), a check valve 12160, a diffuser 12170 (shown in FIG. 13A), a pump fitment 12180, a nozzle (not shown), a nose cone 12200, and an actuator grip 12210. The housing 12110 includes an upper portion 1205 and a bottom portion 1210. The device 1200 additionally includes an extension spring 1215 and a check valve adapter 1220.

Similar to the actuator grip 210 described with regards to FIG. 3, the actuator grip 12210 provides for actuation displacement by the user. The actuator grip 12210 surrounds the Y-junction 12120 and resides within the housing 12110. FIG. 12A shows two finger grip notches 12215 that are designed into the actuator grip 12210 to allow the user to engage the device 1200 with the fingers, for example but not limited to, the index and middle finger. The finger grip notches 12215 allow the user to engage or grip the device in order to cause device 1200 actuation.

More specifically, the actuator grip 12210 includes a guiding feature 1225 that extends along a length of the housing 12110 behind (as illustrated in FIG. 12A) the propellant canister 12140 and captures an end of the propellant canister 12140. In the illustrated example, the end is the bottom of the propellant canister 12140, which is opposite from the end containing the valve for propellant dispersal. The guiding feature 1225 may capture the end of the propellant canister 12140 by folding above or adhering to the end. The propellant canister 12140 is nested within the guiding feature 1225 such that the guiding feature 1225 securely supports the propellant canister 12140. By enveloping a portion of the propellant canister 12140, the guiding feature 1225 is securely coupled to a larger, more rigid surface area of the propellant canister 12140 than when coupled to a narrow surface, such as the propellant valve 15 in the embodiment of device 1. In this configuration, as the user applies downward movement via the finger grip notches 12215 to actuate the device 1200, the guiding feature 1225 transmits the downward force to the propellant canister 12140, thereby actuating the propellant canister 12140. The guiding feature 1225 actuates the propellant canister 12140 in a stable manner and is less likely to lose its physical coupling to the propellant canister 12140.

In one embodiment, the propellant canister 12140 is entirely enclosed within the housing 12110. In one specific embodiment, the propellant canister 12140 is enclosed by the upper portion of the housing 1205, which may be formed during manufacturing from at least two separate parts. The Y-junction 12120 is fixed in place with the bottom housing portion 1210, with the guiding feature 1225 extending upward to establish the position of the propellant canister 12140 with respect to the Y-junction 12120. This structure ensures that the propellant canister 12140 moves relative to the Y-junction 12120 during actuation, to which it is fluidly coupled.

In a similar manner to the conical spring 220 described with regards to FIG. 7, the extension spring 1215 creates an actuation force that ensures a desired order of actuation between the metered dose pump 12130 and the propellant canister 12140. Specifically, during device actuation, the metered dose pump 12130 first delivers liquid pharmaceutical composition to the dose chamber 12150, followed by propellant canister 12140 actuation to expel the liquid pharmaceutical composition. The force of the extension spring 1215 is established to both provide proper order of actuation and enable ease of actuation by users.

The extension spring 1215 is coupled to the housing upper portion 1205 and the actuator grip 12210. As illustrated in FIG. 12A, a first end of the extension spring 1215 couples to a boss 1230 on the housing upper portion 1205, and a second end of the extension spring 1215 couples to a boss 1235 on the actuator grip 12210. In the embodiment of FIG. 12A, the housing upper portion 1205 and the actuator grip 12210 translate relative to one another during actuation of the device 1200. The extension spring 1215 is coupled to each component such that the extension spring 1215 creates a resisting force when the housing upper portion 1205 and the actuator grip 12210 translate away from each other. As previously described, the user activates the device 1200 by, for example, applying an in-line force acting down from the actuator grips 12210, and up from the vial containing the pharmaceutical composition. This applied force actuates both the metered dose pump 12130 of the vial and the propellant canister 12140. As the applied force on the extension spring 1215 increases, a threshold (higher) force to actuate the propellant canister 12140 is achieved after a threshold (lower) force to actuate the metered dose pump 12130 is achieved, such that the applied force first exceeds the threshold force of the metered dose pump 12130. In this configuration, actuation of the device 1200 first activates the metered dose pump 12130 and then activates the propellant canister 12140 such that dose is loaded into the dose chamber 12150 before propellant begins to expel liquid pharmaceutical composition from the device 1200.

In some embodiments, the extension spring 1215 may be used in lieu of or in addition to the conical spring 220. The configuration of the extension spring may streamline the assembly process of the device relative to the configuration of the conical spring, as the conical spring may create a resisting force between the propellant canister 140 and Y-junction 120 such that the components are pushed apart during assembly, whereas the extension spring may pull the components towards each other. In addition, the configuration of the extension spring may prolong the shelf life and overall lifetime of the device relative to the configuration of the conical spring. This may be in part due to the press fit between the stem of the propellant canister 140 and Y-junction 120 of the device 100, which may naturally relax over time and which may be propagated by the resisting force of the conical spring between the propellant canister 140 and Y-junction 120, potentially furthering the decrease in durability of the press fit over time.

The check valve adapter 1220 is an adapter that couples the check valve 12160 and the Y-junction 12120. The check valve 12160 may be an embodiment of check valve 160. In the embodiment of FIGS. 12A-12B, the check valve adapter 1220 is a cylindrical component having a first end that inserts into a channel of the Y-junction 12120 and mates with the check valve 12160 positioned within the channel of the Y-junction 12120 and a second end that mates with the metered dose pump 130. As illustrated in the zoomed-in view in FIG. 12B, an end of the check valve 12160 comprises a flange that is captured at an end of the channel of the Y-junction 12120 and mates with a respective interface of the check valve adapter 1220. The check valve 12160 and/or check valve adapter 1220 may be secured at each end with an adhesive, ultrasonic welding, an interference fit (e.g., press fit, friction fit, or similar), or some combination thereof. The check valve adapter 1220 may augment the function of the check valve 12160 by improving the seal between the check valve 12160 and the Y-junction 12120. As discussed with regards to FIG. 3, a check valve may: (a) reduce or eliminate dose leakage which could occur through the metered dose pump if the pump stem was depressed and the propellant canister was actuated; (b) allow for improved consistency in dose delivery by the device; and/or (c) provide that liquid pharmaceutical composition is not pushed back down an internal dose loading channel of the Y-junction and into the metered dose pump.

FIG. 13A shows a cross section of a diffuser 12170 as seated within the device 1200, according to an additional embodiment. The diffuser 12170 may be an embodiment of the diffuser 170. In this implementation of the device 1200, the diffuser 12170 is annular. As shown in FIG. 13A, the diffuser 12170 sits on a shelf 1305 inside a bore 1310 of the Y-junction 12120, and the dose chamber 12150 is inserted into the bore 1310 of the Y-junction 12120. The diffuser 12170 is seated between the shelf of the bore of the Y-junction 12120 and a bottom face of the dose chamber 12150, sealing against both of those surfaces. The diffuser 12170 may further be sealed along its inner diameter to the Y-junction 12120. In this configuration, the diffuser 12170 creates an interference seal along its inner diameter, its upper face, and its lower outer edge (in contact with the shelf 1305). This configuration may allow expansion of the diffuser 12170, for example, as propellant flows through the diffuser 12170 due to changes in temperature or as a result of device assembly. Sealing the diffuser 12170 along its inner diameter may improve the consistency and/or quality of the seal and/or performance of the diffuser 12170 relative to sealing the diffuser 12170 along its top and bottom faces in a compression fit, which could compress the diffusion path within (the path along which propellant travels and is diffused). In this configuration, variations in the manufacturing of the diffuser 12170 may be less likely to affect the performance of the diffuser 12170. For example, the tolerances of the outer diameter of the diffuser 12170 may not need to be as precisely controlled to prevent bending of the diffuser 12170 such that flatness of the diffuser 12170 is maintained to ensure a proper compression fit along its faces. In some instances, the interference seal may or may not be liquid or gas tight.

FIG. 13B shows an exploded view of the dose chamber 12150 and the Y-junction 12120, according to an additional embodiment. FIG. 13B illustrates the bore 1310 and the shelf 1305 of the Y-junction 12120. The dose chamber 12150 may include a chamfer 1315 around an outer edge of its bottom face such that the dose chamber 12150 may be easily inserted into the bore 1310. In alternate embodiments, the configuration of the dose chamber 12150 and Y-junction 12120 may be reversed such that the dose chamber 12150 includes a bore into which a diffuser and an end of the Y-junction 12120 is inserted.

FIG. 14 illustrates the nose cone 12200, according to an additional embodiment. The nose cone 12200 may be an embodiment of the nose cone 200. As previously described, the external geometries of the nose cone 12200 assist in providing proper alignment of the device 1200 during insertion into the nose. As shown in FIG. 14, the nose cone 12200 comprises an opening 1405 that aligns with the nozzle (not shown). The dose chamber 12150 (not shown in this view) may be positioned between two bosses 1410a, 1410b that maintain the alignment of the dose chamber 12150 and the nozzle within the nose cone 12200. In the embodiment of FIG. 14, the nose cone 12200 is integrated into the design of the clamshells. The nose cone 12200 and the clamshells may be molded together during manufacturing, decreasing the overall part count of the device 1200 and enabling easy assembly of the device 1200.

5.5. Kits

In another aspect, kits are provided for acutely treating migraine with or without aura.

The kit comprises a vial and a device. The vial is sealed, and sealably contains at least one effective dose of a liquid pharmaceutical composition comprising dihydroergotamine (DHE) or salt thereof. The vial is configured to be attachable to the device. The device is reciprocally configured to receive the vial. Upon attachment of the vial to the device by the user, the device becomes a manually actuated, propellant-driven, metered-dose intranasal administration device capable of providing, after intranasal administration of a dose of liquid pharmaceutical composition, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0\text{-}inf}$ of DHE of at least 2500 pg*hr/ml.

In typical embodiments, upon attachment of the vial to the device, the device becomes a manually actuated, propellant-driven, metered-dose intranasal administration device as described in Section 5.3.5.3 above. In currently preferred embodiments, upon attachment of the vial to the device, the device becomes a manually actuated, propellant-driven, metered-dose intranasal administration device as particularly described in Section 5.3.5.3.1 above. In currently preferred embodiments, the propellant-containing canister is a pressurized canister that is sealed within the device and is not accessible to the user.

In various embodiments, the vial is a sealed glass vial. In currently preferred embodiments, the vial is a 3.5-mL amber sealed glass vial.

In typical embodiments, the liquid pharmaceutical composition that is sealably contained within the vial is a liquid pharmaceutical composition as described in Section 5.3.2 above. In currently preferred embodiments, the vial comprises a liquid pharmaceutical composition having the following composition: a clear, colorless to faintly yellow solution in an amber glass vial containing:

| | |
|---|---|
| dihydroergotamine mesylate, USP | 4.0 mg |
| caffeine, anhydrous, USP | 10.0 mg |
| dextrose, anhydrous, USP | 50.0 mg |
| carbon dioxide, USP | qs |
| purified water, USP | qs |
| | 1.0 mL. |

The vial contains liquid pharmaceutical composition in an amount sufficient for at least one total dose of DHE, or salt thereof, to be delivered by the device, in a single undivided or a plurality of divided doses. In particular embodiments, the vial contains liquid pharmaceutical composition in an amount sufficient for at most one total dose of DHE, or salt thereof, to be delivered by the device, in a single undivided or a plurality of divided doses.

In typical embodiments, the propellant canister within the device that is co-packaged with the vial in the kit contains pressurized propellant in an amount sufficient for optional priming of the device followed by delivery of at least one total dose of DHE, or salt thereof, to be delivered by the device either in a single undivided or a plurality of divided doses. In particular embodiments, the propellant canister contains pressurized propellant in an amount sufficient for optional priming of the device followed by delivery of at most one total dose of DHE, or salt thereof, to be delivered by the device, in a single undivided or a plurality of divided doses.

5.6. Experimental Examples

The invention is further described through reference to the following experimental examples. These examples are provided for purposes of illustration only, and are not intended to be limiting.

5.6.1. Example 1: Reproducibility of Dose Delivery

Table 2 provides experimental data on one implementation of the in-line device described in Section 5.3.5.1.1 above. As used in Table 2, "dose" refers to a volume delivered in a single device actuation.

TABLE 2

| | Dose Volume [µL] | | | | | | | |
|---|---|---|---|---|---|---|---|---|
| Shot # | Device 1 | Device 2 | Device 3 | Device 4 | Device 5 | Device 6 | | |
| 1 | 190.6 | 193.7 | 185.3 | 199.2 | 199.2 | 145.1 | 185 uL + 10% | 203.5 |
| 2 | 181.4 | 205.5 | 178.9 | 167.7 | 167.7 | 141.7 | 185 uL − 10% | 166.5 |
| 3 | 183.1 | 188.5 | 173.3 | 165.6 | 165.6 | 138.5 | 185 uL + 15% | 212.8 |
| 4 | 183.2 | 193.3 | 145.8 | 164.6 | 164.6 | 136.6 | 185 uL − 15% | 157.3 |
| 5 | 183.3 | 201.5 | 200.7 | 162.0 | 162.0 | 142.1 | | |
| 6 | 185.8 | 207.7 | 166.3 | 179.4 | 179.4 | 138.9 | | |
| 7 | 184.3 | 195.1 | 180.3 | 164.8 | 164.8 | 140.9 | | |
| 8 | 183.3 | 205.4 | 175.3 | 164.9 | 164.9 | 142.0 | | |
| 9 | 180.5 | 178.1 | 172.0 | 164.1 | 164.1 | 141.8 | | |
| 10 | 179.7 | 204.0 | 178.0 | 170.6 | 170.6 | 143.9 | | |
| Mean | 183.5 | 197.3 | 175.6 | 170.3 | 170.3 | 141.2 | | |
| StDev | 3.1 | 9.3 | 14.0 | 11.3 | 11.3 | 2.5 | | |
| Min | 179.7 | 178.1 | 145.8 | 162.0 | 162.0 | 136.6 | | |
| Max | 190.6 | 207.7 | 200.7 | 199.2 | 199.2 | 145.1 | | |

5.6.2. Example 2: Phase I Clinical Trial

A Phase I clinical trial was conducted to compare the bioavailability of dihydroergotamine (DHE) mesylate following (i) single divided dose intranasal administration of INP104, a drug-device combination employing a Precision Olfactory Delivery (POD®) Device (Impel NeuroPharma, Seattle); (ii) intranasal administration of Migranal® Nasal Spray (Valeant Pharmaceuticals); and (iii) intravenous injection with D.H.E. 45® (Valeant Pharmaceuticals) in healthy adult subjects.

5.6.2.1. Study Design

The study was a three-period, three-way, randomized, open-label, single-dose, cross-over, comparative bioavailability study.

Thirty-six subjects (approximately equal numbers of men and women) were enrolled and randomized into the study. Twenty-eight subjects completed the study. Treatment assignment was randomized in a three-treatment, three-period balanced crossover study of six sequences shown below, with a 7-day washout between treatments:

TABLE 3

| | Treatment | | |
|---|---|---|---|
| Sequence | 1 | 2 | 3 |
| 1 | A | B | C |
| 2 | B | C | A |
| 3 | C | A | B |

TABLE 3-continued

| Sequence | Treatment | | |
|---|---|---|---|
| | 1 | 2 | 3 |
| 4 | A | C | B |
| 5 | B | A | C |
| 6 | C | B | A |

A = 1.45 mg INP104
B = 1.0 mg D.H.E. 45, IV
C = 2 mg Migranal ® Nasal Spray.
Subjects all received 10 mg IV metoclopramide 5-10 minutes prior to each treatment.

INP104 was self-administered using the I123 POD™ Device (Impel NeuroPharma, Seattle). The dose of DHE mesylate was divided, with one spray in each nostril delivering a total target dose of 1.45 mg DHE mesylate.

The I123 POD Device is a handheld, manually actuated, propellant-driven, metered-dose administration device intended to deliver a drug formulation to the nasal cavity. Drug delivery to the nasal cavity via the I123 POD Device is driven by hydrofluoroalkane-134a (HFA) propellant. The I123 POD Device functions as an intranasal delivery device; the HFA propellant in the I123 POD Device is not intended to deliver drug to the lungs and does not contact the DHE formulation until the time of delivery.

The INP104 drug component, DHE DP, is a 3.5-mL amber glass vial filled with DHE mesylate 4 mg/mL. The formulation is identical to that in the Migranal® Nasal Spray device: a clear, colorless to faintly yellow solution in an amber glass vial containing:

| | |
|---|---|
| dihydroergotamine mesylate, USP | 4.0 mg |
| caffeine, anhydrous, USP | 10.0 mg |
| dextrose, anhydrous, USP | 50.0 mg |
| carbon dioxide, USP | qs |
| purified water, USP | qs |
| | 1.0 mL. |

The DHE DP vial attaches to the I123 POD Device. The I123 POD Device may have a nominal output between 175 µL/actuation pump and 205 µL/actuation pump (inclusive). In some embodiments, the I123 POD Device may have a nominal output that is about 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, or 205 µL/actuation pump.

A single manual actuation of the device by the user results in the operation of the metering pump to fill the dose chamber with the DHE formulation and subsequent, but almost instantaneous, activation of the propellant canister to expel the formulation through the nozzle, as a spray, resulting in delivery to the nasal cavity of the user. The device is designed to be disposed of after successful single divided-dose drug delivery (1 spray per nostril). Actuation of the I123 POD Device releases approximately 63 µL of HFA-134a propellant, similar to HFA exposure from metered-dose inhalers.

D.H.E. 45® (Valeant Pharmaceuticals, NDA 005929) was administered in a volume of 1 mL intravenously over 1 minute.

Migranal® (Valeant Pharmaceuticals, NDA 20148) Nasal Spray (2 mg) was self-administered with equal dosing to both nostrils. In accordance with the product label, one spray (0.5 mg) was administered in each nostril initially, followed by an additional spray (0.5 mg) in each nostril 15 minutes later.

5.6.2.2. Pharmacokinetic Assessments
Sampling and Processing

Blood samples for PK analysis were obtained, according to the clinical trial site's standard operating procedures (SOPs), within 15 minutes prior to dosing and at 5, 10, 20, 30, 40 and 50 minutes, and 1, 1.25, 1.5, 1.75, 2, 3, 4, 8, 12, 24, 36 and 48 hours after dosing. For the Migranal® Nasal Spray dose, the PK sampling timeclock was started following administration of the first dose of Migranal® Nasal Spray.

Pharmacokinetic Analysis

Individual DHE and 8'-OH-DHE plasma concentration data were listed for each individual and summarized by nominal sampling time-point and administration method with descriptive statistics (sample size [N], arithmetic mean, standard deviation [SD], median, minimum, maximum and geometric mean). Individual and mean DHE and 8'-OH-DHE plasma concentration-time profiles for each administration method were also graphed.

Pharmacokinetic parameters were computed from the individual plasma DHE and 8'-OH-DHE concentrations using a non-compartmental approach. Appropriate validated PK software (e.g., Phoenix WinNonlin v6.3) was used. The parameters that were determined and their definitions are provided in Table 4 below.

TABLE 4

| | |
|---|---|
| $C_{max}$ | Maximum observed drug concentration. |
| $T_{max}$ | Time to maximum observed drug concentration. If the maximum value occursat more than one time-point, $T_{max}$ is defined as the first time point with this value. |
| $AUC_{0-t}$ | Area under the drug concentration-time curve, calculated using linear-up log-down trapezoidal summation from time zero to the time of the last Measurable concentration. |
| $k_{el}$ | Apparent terminal elimination rate constant, calculated by linear regression of the terminal linear portion of the log concentration vs. time curve. |
| $AUC_{0-inf}$ | Area under the drug concentration-time curve from time zero to infinity, calculated as $AUC_{0-t} + Ct/k_{el}$. |
| $t_{1/2}$ | Apparent elimination half-life, calculated as $\ln(2)/k_{el}$. |
| CL/F (CL for i.v.) | Apparent clearance calculated as $Dose/AUC_{0-inf}$. |
| Vz/F (Vz for i.v.) | Apparent volume of distribution at the terminal phase, calculated as $Dose/(e_1 * AUC_{0-inf})$. |

Statistical Methods for Pharmacokinetic Analyses

PK parameters were summarized by administration method using descriptive statistics (arithmetic means, SD, coefficients of variation [CV], sample size [N] minimum, maximum, median and geometric mean). Geometric mean was calculated for $AUC_{0-t}$, $AUC_{0-inf}$ and $C_{max}$.

No value for $k_{el}$, $t_{1/2}$, $AUC_{0-inf}$, CL/F, Vz/F, as appropriate, were reported for cases that did not exhibit a terminal log-linear phase in the concentration versus time profile or did not contain sufficient data during this phase for parameter estimation.

Statistical Analysis

A comparative bioavailability assessment was undertaken to demonstrate (i) that the lower 90% confidence interval of the DHE after INP104 to DHE after Migranal Nasal Spray geometric mean ratios for $C_{max}$ and AUC ($AUC_{0-t}$, $AUC_{0-inf}$) is not less than 80%, and (ii) the upper 90% confidence interval of the DHE after INP104 to D.H.E. 45 Injection (IV) geometric mean ratios for $C_{max}$ and AUC ($AUC_{0-t}$, $AUC_{0-inf}$) not greater than 125%—i.e., to demonstrate that exposure is equal to or greater than 80% and equal to or less than 125% range observed between Migranal Nasal Spray and D.H.E. 45 Injection (IV), respectively.

For each comparator (Migranal Nasal Spray and D.H.E. 45 Injection (IV)), the following analysis methods were performed independently. Analysis of variance (ANOVA) with effects for sequence, subject nested within sequence, period, and treatment were performed on the ln-transformed DHE and 8'OH-DHE $AUC_{0-t}$, $AUC_{0-inf}$ and $C_{max}$. Each ANOVA included calculation of least squares mean (LSM), the difference between administration method LSM, and the standard error associated with the difference.

Only subjects who had completed all three treatments and had sufficient PK sample collection to generate the key PK parameters ($AUC_{0-t}$, $AUC_{0-inf}$ and $C_{max}$) for each administration method were included in the ANOVA analysis.

Ratios of geometric means were calculated using the exponentiation of the difference between treatment LSM from the analyses on the ln-transformed $AUC_{0-t}$, $AUC_{0-inf}$ and $C_{max}$. These ratios were expressed as a percentage relative to the reference (comparator) treatment, i.e. INP104 [test]/Comparator [reference]. Consistent with the two one-sided tests for bioequivalence, 90% confidence intervals were obtained for the ratio of the geometric means for $AUC_{0-t}$, $AUC_{0-inf}$ and $C_{max}$.

5.6.2.3. Results: DHE and 8'OH-DHE Pharmacokinetics

The time course of plasma DHE concentrations is plotted in FIGS. 10A and 10B, and initial summary statistics are provided in Table 5 below.

TABLE 5

DHE pharmacokinetics

|  | Migranal ® (2 mg intranasal) | INP104 (1.45 mg intranasal) | D.H.E. 45 ® (1 mg IV) |
|---|---|---|---|
| $AUC_{0-inf}$ (pg*hr/ml) mean [% CV] (range) | 2,248 [68%] (444-7247) | 6,291 [44%] (978-10,445) | 10,053 [18%] |
| $C_{max}$ (pg/ml) mean [% CV] (range) | 318 [83%] (25.4-1190) | 1,258 [54%] (270-2660) | 14,460 [34%] |
| $T_{max}$ (min) mean | 55 | 34 | 5 |
| $T_{max}$ (hr) mean (range) | 0.92 (0.5-3.08) | 0.57 (0.333-2.05) | 0.08 |

As compared to Migranal® Nasal Spray, INP104 provides nearly 3-fold higher mean systemic drug exposure, with an $AUC_{0-inf}$ of 6,291 pg*hr/ml as compared to 2,248 pg*hr/ml for Migranal®. INP104 also provides nearly 4-fold higher mean maximal plasma concentration, with a $C_{max}$ of 1,258 pg/ml as compared to 318 pg/ml for Migranal®. Maximal DHE plasma concentration is reached faster with INP104, with a mean $T_{max}$ of 34 minutes versus 55 minutes for Migranal®. The higher systemic drug exposure and higher maximal plasma concentration were achieved with a lower administered dose of the identical formulation of DHE mesylate, 1.45 mg for INP104 versus 2.0 mg for Migranal®, and without requiring a 15-minute wait between administration of divided sub-doses, as required for Migranal®.

In addition, systemic delivery of DHE was more consistent with INP104 than with Migranal®, with lower variation observed across subjects for both $AUC_{0-inf}$ and $C_{max}$ parameters (see Table 5 above for coefficients of variation).

Although bolus intravenous administration of 1 mg DHE mesylate provided greater than 10-fold higher $C_{max}$ than 1.45 mg DHE mesylate administered intranasally by INP104, the high $C_{max}$ achieved with intravenous administration is known to be correlated with adverse events ("AE"s), specifically nausea, and IV DHE mesylate (D.H.E. 45) is most commonly administered with an anti-emetic. Within 20-30 minutes following administration, DHE plasma concentrations achieved through INP104 intranasal administration were essentially indistinguishable from concentrations achieved by intravenous administration. Thus, despite a greater than 10-fold higher $C_{max}$, bolus intravenous administration of 1 mg DHE mesylate provided less than 2-fold greater systemic drug delivery, measured as $AUC_{0-inf}$, as compared to INP104 intranasal delivery.

The 8'OH-DHE metabolite of DHE is known to be active, and to contribute to the long-lasting effect of DHE on migraine. The time course of plasma 8'-OH-DHE concentrations is plotted in FIGS. 11A and 11B. Initial summary statistics for plasma concentrations of 8'OH-DHE are provided in Table 6, below.

TABLE 6

8'OH-DHE pharmacokinetics

|  | Migranal ® (2 mg intranasal) | INP104 (1.45 mg intranasal) | D.H.E. 45 ® (1 mg IV) |
|---|---|---|---|
| $AUC_{0-inf}$ (pg*hr/ml) [% CV] | 1113 [53%] n = 6 | 1063 [59%] n = 20 | 924 [63%] n = 28 |
| $C_{max}$ (pg/ml) [% CV] | 42 [35%] n = 8 | 58 [44%] n = 24 | 392 [26%] n = 28 |
| $T_{max}$ (hr) | 2.30 [57%] n = 8 | 1.43 [53%] n = 24 | 0.08 [8%] n = 28 |

These data demonstrate that intranasal administration of 1.45 mg DHE by INP104 provides equivalent systemic exposure to the active metabolite of DHE as bolus intravenous administration of 1.0 mg DHE. In addition, the metabolite was detected in only 8 subjects after Migranal® intranasal delivery, versus 24 subjects following intranasal administration of INP104.

6. INCORPORATION BY REFERENCE

The disclosures of each and every patent, patent application, and publication cited herein are hereby incorporated by reference in their entirety.

7. EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of acutely treating migraine headache with or without aura, comprising:
   administering, via a manually actuated, metered-dose, propellant-driven intranasal delivery device, to a subject with migraine headache an effective dose of a liquid pharmaceutical composition comprising 4 mg/mL of dihydroergotamine (DHE) mesylate,
   wherein the effective dose comprises 1.45 mg of DHE mesylate administered as two divided doses of one spray per each nostril without requiring a timed wait between the two divided doses, and
   wherein the manually actuated, metered-dose, propellant-driven intranasal delivery device is configured to sequentially release the liquid pharmaceutical composition followed by propellant, and wherein, following administration of the dose, the mean DHE $C_{max}$ in plasma is at least 750 pg/ml; the time to $C_{max}$ ($T_{max}$) of DHE in plasma is less than 45 minutes; and the mean plasma $AUC_{0-inf}$ of DHE is at least 2500 pg*hr/ml.

2. The method of claim 1, wherein, following administration of the dose, the mean plasma $AUC_{0-inf}$ of DHE is at least 6000 pg*hr/ml.

3. The method of claim 1, wherein, prior to first manual actuation, the liquid pharmaceutical composition and propellant are not in contact within the device.

4. The method of claim 1, wherein each manual actuation brings a metered volume of liquid pharmaceutical composition and a separately metered volume of propellant into contact within a dose chamber of the device.

5. The method of claim 4, wherein contact of propellant with liquid pharmaceutical composition within the dose chamber of the device creates a spray of liquid pharmaceutical composition as the formulation is expelled through a nozzle of the device.

* * * * *